(12) United States Patent
Otawara

(10) Patent No.: US 8,092,375 B2
(45) Date of Patent: Jan. 10, 2012

(54) ENDOSCOPE INSERTION PORTION WITH PLURALITY OF OBSERVATION WINDOWS

(75) Inventor: Takashi Otawara, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1224 days.

(21) Appl. No.: 11/825,063

(22) Filed: Jul. 3, 2007

(65) Prior Publication Data

US 2007/0260119 A1   Nov. 8, 2007

Related U.S. Application Data

(63) Continuation of application No. PCT/JP2006/300101, filed on Jan. 6, 2006.

(30) Foreign Application Priority Data

Jan. 7, 2005 (JP) ................... 2005-003201

(51) Int. Cl.
A61B 1/015 (2006.01)
A61B 1/00 (2006.01)

(52) U.S. Cl. ......... 600/157; 600/129; 600/168; 600/176

(58) Field of Classification Search ............ 600/129, 600/113, 156, 157, 168, 172, 173, 176, 160
See application file for complete search history.

(56) References Cited

U.S. PATENT DOCUMENTS

| | | | | |
|---|---|---|---|---|
| 4,667,656 A | * | 5/1987 | Yabe | 600/109 |
| 5,630,795 A | | 5/1997 | Kuramoto et al. | |
| 5,782,751 A | * | 7/1998 | Matsuno | 600/157 |
| 6,217,510 B1 | | 4/2001 | Ozawa et al. | |
| 6,866,627 B2 | * | 3/2005 | Nozue | 600/127 |
| 7,062,311 B1 | * | 6/2006 | Sendai et al. | 600/407 |
| 7,267,647 B2 | * | 9/2007 | Okada et al. | 600/166 |
| 7,491,166 B2 | * | 2/2009 | Ueno et al. | 600/107 |
| 2002/0177780 A1 | * | 11/2002 | Sendai | 600/476 |
| 2004/0122290 A1 | * | 6/2004 | Irion et al. | 600/171 |
| 2004/0158129 A1 | * | 8/2004 | Okada et al. | 600/168 |
| 2006/0069306 A1 | * | 3/2006 | Banik et al. | 600/118 |

FOREIGN PATENT DOCUMENTS

EP    1834570 A1    9/2007

(Continued)

OTHER PUBLICATIONS

Machine translation of JP 06-154155, Jun. 3, 1994.*

(Continued)

*Primary Examiner* — John P Leubecker
(74) *Attorney, Agent, or Firm* — Scully, Scott, Murphy & Presser, P.C.

(57) ABSTRACT

An endoscope insertion portion of the invention includes a plurality of observation windows having different outer diameters for leading incident light to a plurality of image pickup portions, and disposed on a distal end surface of the distal end portion; and an air/water feeding portion for spouting out a gas or liquid toward the plurality of observation windows, and disposed to the distal end portion. One of the plurality of observation windows having the largest outer diameter is disposed on the distal end surface at a position closest to the air/water feeding portion than the other of the plurality of observation windows.

10 Claims, 12 Drawing Sheets

FOREIGN PATENT DOCUMENTS

| | | |
|---|---|---|
| EP | 1834571 A1 | 9/2007 |
| EP | 1834573 A1 | 9/2007 |
| JP | 06-154155 | 6/1994 |
| JP | 11-104070 | 4/1999 |
| JP | 11-510615 | 9/1999 |
| WO | WO 96/39916 | 12/1996 |

OTHER PUBLICATIONS

Extended European Search Report mailed Dec. 22, 2010, from the European Patent Office in counterpart European Patent Application No. 06702032.

* cited by examiner

ENDOSCOPE INSERTION PORTION WITH PLURALITY OF OBSERVATION WINDOWS

CROSS REFERENCE TO RELATED APPLICATION

This application is a continuation application of PCT/JP2006/300101 filed on Jan. 6, 2006 and claims benefit of Japanese Application No. 2005-003201 filed in Japan on Jan. 7, 2005, the entire contents of which are incorporated herein by this reference.

BACKGROUND OF THE INVENTION

1. Field of the Invention

The present invention relates to an endoscope insertion portion of an endoscope having a plurality of observation optical systems.

2. Description of the Related Art

Conventionally, endoscopes have been widely used in the medical field and the like. With an endoscope, for example, internal organs in a body cavity can be observed by inserting an elongated insertion portion into the body cavity, and various treatments can be performed using a treatment instrument inserted into a treatment instrument insertion channel as necessary. At a distal end of the insertion portion, a bending portion is provided. By operating an operation portion of the endoscope, observing direction of an observation window at a distal end portion can be changed.

In general, an endoscope is provided with an air/water feeding nozzle for cleaning for a case where body fluid or the like adheres on an outer surface of the objective optical system of the endoscope to disturb the observation when the endoscope is inserted into the body cavity. The outer surface of the objective optical system of the endoscope can be secured of a clean observation field of view with, for example, a cleaning liquid spouted out or air sprayed from the air/water feeding nozzle.

Further, an endoscope is used to observe the inside of the body cavity where little natural light enters. Therefore, in an endoscope, to obtain photographing light to be taken in from an observation window, illumination light led by a light guide or the like is irradiated into the body cavity from an illumination window.

For example, an endoscope having a plurality of objective optical systems is proposed as described in Japanese unexamined patent publication No. 06-154155. This endoscope has a plurality of image pickup units, wherein the plurality of objective optical systems and an aperture of an air/water feeding nozzle are located at a distal end of an insertion portion to line up on a generally straight line.

As mentioned above, it is desirable for an endoscope to have a large observation window, that is, to increase lens diameter of the object optical system, in order to obtain enough photographing light level by illumination light from an illumination window in the body cavity where little natural light enters, so that fine observation can be performed.

SUMMARY OF THE INVENTION

To achieve the above-described objects, an endoscope insertion portion according to the present invention is inserted into a body cavity and includes a distal end portion at a distal end part, the endoscope insertion portion including: a plurality of observation windows having different outer diameters for leading incident light to a plurality of image pickup portions, and disposed on a distal end surface of the distal end portion; and an air/water feeding portion for spouting out a gas or liquid toward the plurality of observation windows, and disposed to the distal end portion, wherein one of the plurality of observation windows having the largest outer diameter is disposed on the distal end surface at a position closest to the air/water feeding portion than the other of the plurality of observation windows.

DETAILED DESCRIPTION OF THE PREFERRED EMBODIMENT(S)

First Embodiment

Figure 1:
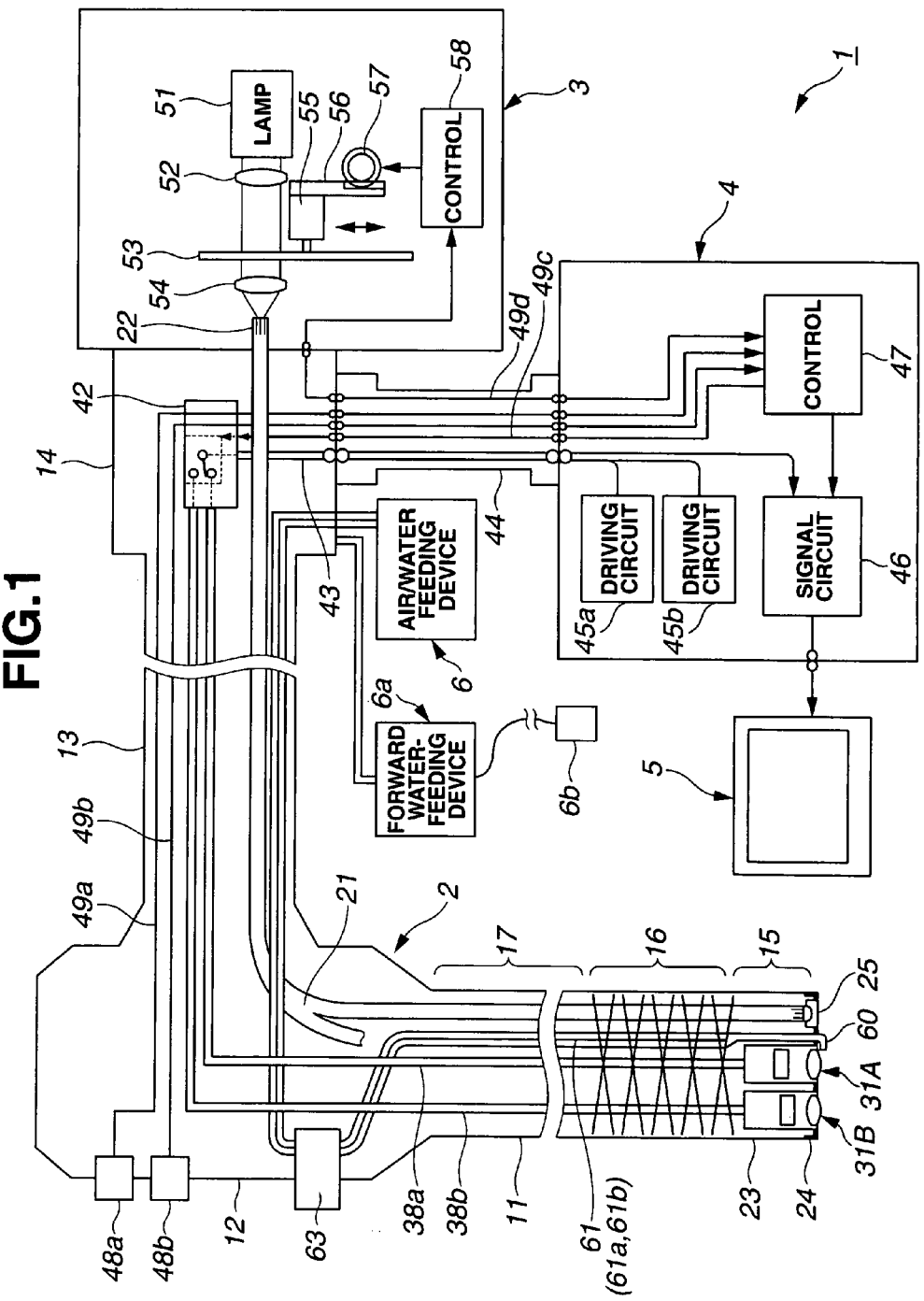
FIG. 1 is an illustrative view schematically showing an endoscope system.

Referring to the drawings, an embodiment of the present invention is described below.

First, based on FIG. 1, configuration of an endoscope system according to the present embodiment is described. FIG. 1 is an illustrative view schematically showing a configuration of the endoscope system according to the first embodiment of the present invention.

As shown in FIG. 1, an endoscope system 1 of the present embodiment includes: an endoscope 2 capable of performing normal light observation and fluorescent light observation; a light source device 3 for supplying illumination light to the endoscope 2; a processor 4 serving as a signal processing device for performing signal processing for the endoscope 2; a monitor 5 which is inputted with a video signal outputted from the processor 4 to display an endoscope image for normal observation or fluorescent light observation; an air/water feeding device 6 for feeding air and water; and a forward water-feeding device 6a for forwardly feeding water.

The endoscope 2 includes: an endoscope insertion portion (hereinafter simply referred to as insertion portion) 11 elongated to facilitate insertion into a body cavity; an operation portion 12 connected to a proximal end of the insertion portion 11; and a universal cable 13 extending from a side portion of the operation portion 12. A connector 14 provided to an end portion of the universal cable 13 is detachably connected to the light source device 3.

The insertion portion 11 of the endoscope 2 includes: a rigid distal end portion 15 formed at a distal end of the insertion portion 11; a bending portion 16 formed at a proximal end of the distal end portion 15; and a flexible tube portion 17 having flexibility formed from the proximal end of the bending portion 16 to the operation portion 12.

In the insertion portion 11, a light guide 21 for transmitting illumination light is inserted. The light guide 21 is inserted into the universal cable 13 via the operation portion 12, and has a proximal end portion 22 connected to a light guide connector not shown protruding from the connector 14.

A distal end part of the light guide 21 is fixed in the distal end portion 15. Note that at the distal end part of the distal end portion 15 is disposed an illumination lens 25 of an illuminating unit described below which is an illumination optical system, and illumination light is radiated from the light guide 21 via the illumination lens 25. On a distal end surface of the distal end portion 15, a distal end cover 24 is provided.

Note that, in the present embodiment, the light guide 21 is inserted in the insertion portion 11, being, for example, diverged in the operation portion 12 to be split twofold in the insertion portion 11. Distal end surfaces of the respective light guides 21 split twofold are each located near rear surfaces of the two illumination lenses 25 provided on the distal end cover 24.

Also, in the insertion portion 11 is provided a treatment instrument channel (also referred to as forceps channel) which is a first duct (omitted in FIG. 1) for rendering a treatment instrument such as a forceps insertable into the insertion portion 11. A distal end of the treatment instrument channel has an aperture at a distal end surface of the distal end cover 24.

The treatment instrument channel diverges near the proximal end of the insertion portion 11. One of the diverged treatment instrument channels is inserted up to a treatment instrument insertion port not shown disposed to the operation portion 12. The other of the diverged treatment instrument channels communicates with a suction channel in through the insertion portion 11 and the universal cable 13, with a proximal end being connected to an absorbing portion not shown serving as absorbing means via the connector 14.

In the distal end portion 15, two image pickup units are disposed. In the present embodiment, there are incorporated a normal-light-observing image pickup unit (hereinafter referred to as normal light image pickup unit) 31A which is a first image pickup portion configuring first image pickup means for normal light observation, and a fluorescent-light-observing image pickup unit (hereinafter referred to as fluorescent light image pickup unit) 31B which is a second image pickup portion configuring second image pickup means for special observation.

Note that the second image pickup portion configuring the second image pickup means, which in the present embodiment is a fluorescent-light-observing image pickup unit capable of performing fluorescent light observation which is a special observation, may be, for example, an image pickup unit for night vision observation, an image pickup unit for infrared observation, or the like, and is not limited to use for fluorescent light observation in particular.

To the normal light image pickup unit 31A and the fluorescent light image pickup unit 31B, respective one ends of a signal cables 38a, 38b are connected. Respective other ends of the signal cables 38a, 38b are inserted into the operation portion 12 and the universal cable 13, and are switchably connected to a common signal cable 43 in a relay board 42 provided in the connector 14.

The common signal cable 43 is connected to a processor 4 in through a scope cable 44 connected to the connector 14.

In the processor 4, there are provided driving circuits 45a, 45b for respectively driving image pickup devices of the normal light image pickup unit 31A and the fluorescent light image pickup unit 31B; a signal processing circuit 46 for performing signal processing to image pickup signals respectively outputted from the two image pickup devices via the relay board 42; and a control circuit 47 for controlling operation state of the signal processing circuit 46 or the like.

Also, the operation portion 12 of the endoscope 2 is provided with control switches 48a, 48b; an air/water feeding button 63; a bending operation knob not shown; a switch not shown (also referred to as tele-zoom button) for performing tele-zoom operation of the normal light image pickup unit 31A; a forward water-feeding button not shown; and the above-described treatment instrument insertion port (not shown).

The control switches 48a, 48b are connected to the control circuit 47 of the processor 4 via signal lines 49a, 49b, respectively. In the present embodiment, for example, the control switch 48a generates a signal for switching instruction, and the control switch 48b generates, for example, a signal for freezing instruction.

The relay board 42 performs, responsive, for example, to operation of the control switch 48a, a switching operation such that, from a state where one of the signal cables 38a, 38b respectively connected to the image pickup devices is connected to the common signal cable 43, the other signal cable is connected to the signal cable 43.

Specifically, for example, by operating the control switch 48a, a switching signal is outputted to the relay board 42 via a switching signal line 49c which is inserted in the scope cable 44 and electrically connected to the control circuit 47. The relay board 42 connected with the switching signal line 49c is configured such that an input terminal for signals from the control circuit 47 is normally in L (LOW) level, with a switching control terminal pulled down, and in this state, the signal cable 38a of the normal light image pickup unit 31A is connected to the common signal cable 43. Also in an activation starting state, the switching control terminal is in the L level. That is, unless a switching instruction is performed, the relay board 42 is set to a normal light observation state.

When a user operates the control switch 48a in this state, a control signal is applied by which a signal from the control circuit 47 becomes H (HIGH) level at the input terminal of the relay board 42 via the switching signal line 49c. Then, the relay board 42 pulls up the switching control terminal, and in this state, the signal cable 38b of the fluorescent light image pickup unit 31B is connected to the common signal cable 43.

When the control switch 48a is further operated, the switching control terminal is supplied with an L level signal, and the signal cable 38a of the normal light image pickup unit 31A is connected to the common signal cable 43.

With the operation of the control switch 48a, the control circuit 47 sends a control signal also to the control circuit 58 in the light source device 3 via the control signal line 49d in the scope cable 44. Then, in response to the control signal, the control circuit 58 controls to obtain a state of generating normal observation light or excitation light for fluorescent light observation. Further, the control circuit 47 controls operation state of the signal processing circuit 46 so that the same is operated corresponding to respective image pickup devices of the normal light image pickup unit 31A and the fluorescent light image pickup unit 31B.

The light source device 3 includes: a lamp 51 for generating white light including wavelength of the excitation light; a collimator lens 52 for bringing light of the lamps 51 into a parallel luminous flux; a rotary filter 53 disposed in an optical path of the collimator lens 52, and provided in a circuit direction with an RGB filter that respectively pass lights of wavelength bands of R (RED), G (GREEN) and B (BLUE) in visible light wavelength band (380 to 780 nm), for example; and a condensing lens 54 for condensing transmission light of the rotary filter 53 and radiates the light to the proximal end portion 22 of the light guide 21.

The rotary filter 53 provided with the RGB filter is also provided, on an outside of the circuit direction, with an excitation light filter for passing excitation light with a wavelength band shorter than that of visible light. The rotary filter 53 is rotatably driven by a motor 55. Further, the motor 55 is mounted to a rack 56 and can be moved in a direction orthogonal to an illumination optical axis as shown in an arrow, by means of a gear-equipped motor 57 engaging with the rack 56.

The gear-equipped motor 57 is controlled by a control circuit 58. The control circuit 58 is connected to the control circuit 47 of the processor 4 via the control signal line 49d, and is operated by the control switch 48a to perform a corresponding control operation.

On the distal end portion 15, there is also located an air/water feeding nozzle 60 which is an air/water feeding portion configuring air/water feeding means such that a spouting port thereof faces outer surfaces of respective object lenses (hereinafter also referred to as observation lenses) of the normal light image pickup unit 31A and the fluorescent light image pickup unit 31B located on the distal end cover 24.

The air/water feeding nozzle 60 is connected to an air/water feeding duct 61 whose distal end sides are joined to unite, as described below. A proximal end side of the air/water feeding duct 61 diverges into an air feeding duct 61a and a water feeding duct 61b.

The air feeding duct 61a and the water feeding duct 61b communicating with the air/water feeding nozzle 60 are inserted up to the connector 14 of the universal cable 13, and connected to the air/water feeding device 6 incorporating a pump not shown for feeding air and water.

The air feeding duct 61a and the water feeding duct 61b are interposed with the above-described air/water feeding button 63 in the operation portion 12 present at a halfway of the ducts. Air and water are fed by operating the air/water feeding button 63.

This causes the air/water feeding nozzle 60 to blow a gas such as air or a liquid such as distilled water to outer, surfaces of respective object lenses of the normal light image pickup unit 31A and the fluorescent light image pickup unit 31B located in a spouting direction, so as to remove and clean off body fluid, accretion or the like so that image pickup and observation field of view can be ensured in a clean state.

The insertion portion 11 is also provided inside with a forward water-feeding channel (omitted in FIG. 1) which is a second duct for feeding a liquid such as distilled water to a region to be inspected in the body cavity. A distal end of the forward water-feeding channel has an aperture on a distal end surface of the distal end cover 24.

The forward water-feeding channel is connected to the forward water-feeding device 6a, and interposed with a forward water-feeding button not shown disposed to the operation portion 12. When the forward water-feeding button is operated, a liquid such as distilled water is sprayed from the distal end surface of the insertion portion 11 toward an insertion direction into the body cavity. By this, body fluid or the like adhered to a region to be inspected in the body cavity can be cleaned. Note that, as shown in FIG. 1, a cable extending from the forward water-feeding device 6a is connected with a foot switch 6b. Also by operating the foot switch 6b, a user can spray a liquid such as distilled water toward the insertion direction into the body cavity from the distal end surface of the insertion portion 11.

Further, the above-mentioned treatment instrument channel and the forward water-feeding channel configure an endoscope duct in the present embodiment.

Figure 2:
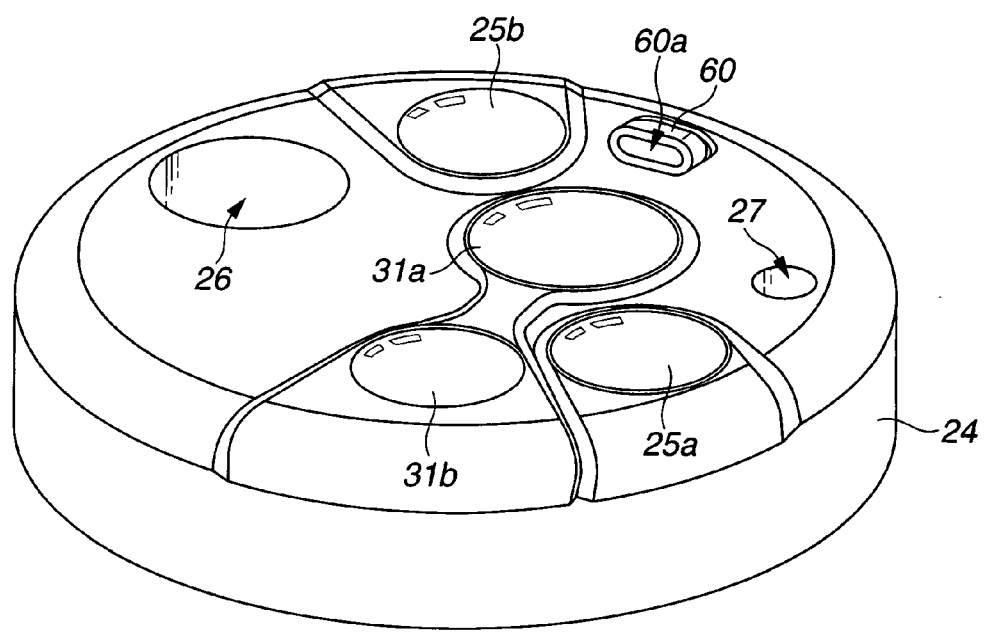
FIG. 2 is a perspective view showing a distal end cover of an endoscope.
Figure 3:
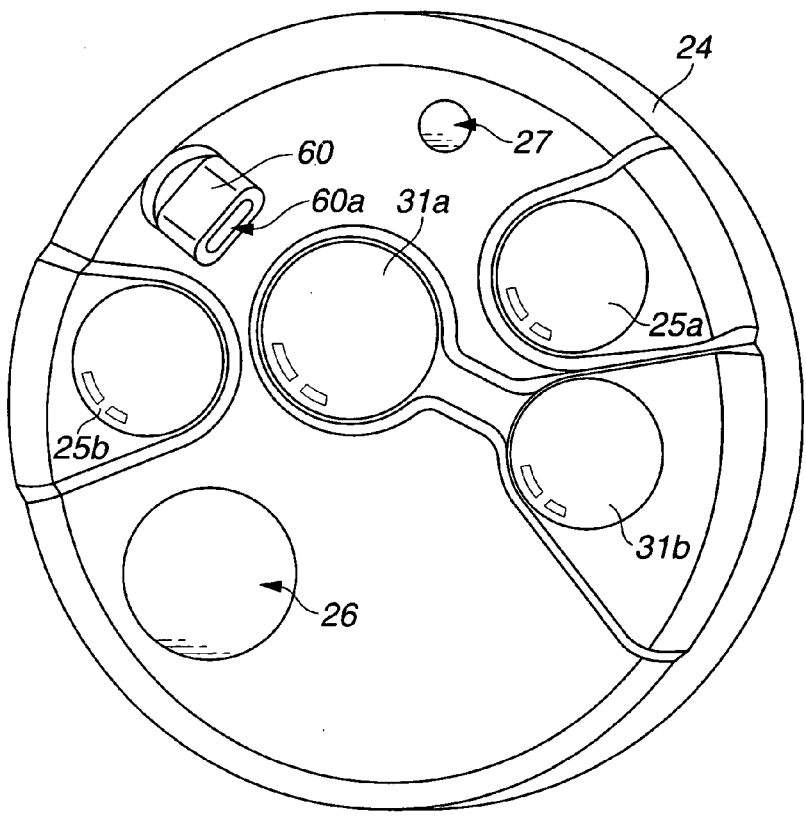
FIG. 3 is a perspective view showing the distal end cover of the endoscope.
Figure 4:
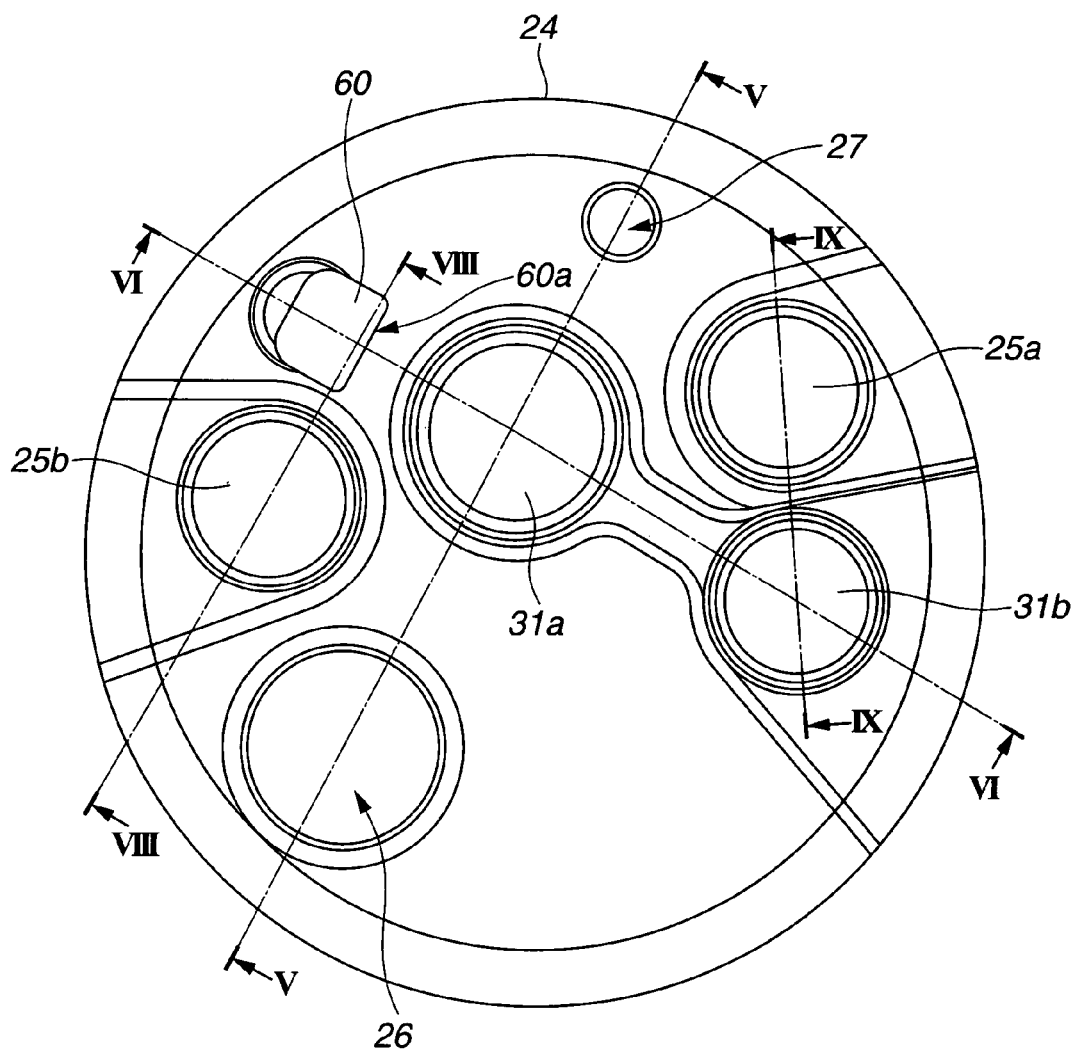
FIG. 4 is a plan view of the distal end cover as viewed from the front.

As shown in FIGS. 2 to 4, on the distal end cover 24 disposed to the distal end portion 15 of the insertion portion 11, there are disposed: an observation lens 31a which is a first observation window of the normal light image pickup unit 31A; an observation lens 31b which is a second observation window of the fluorescent light image pickup unit 31B; two illumination lenses 25a, 25b; an aperture portion 26 of the treatment instrument channel; and an aperture portion 27 of the forward water-feeding channel. On the distal end cover 24, the air/water feeding nozzle 60 is located such that a spouting port 60a faces the observation lenses 31a, 31b, as described above.

Note that FIGS. 2 and 3 are each a perspective view showing the distal end cover part of the endoscope, and FIG. 4 is a plan view of the distal end cover as viewed from the front. The two observation lenses 31a, 31b are optical members.

Specifically, an observation lens 31a is disposed at the generally center of the distal end surface of the distal end cover 24 in a generally circle shape when the distal end portion 15 is viewed from the distal end. Further, on the distal end surface of the distal end cover 24, the illumination lenses 25a and 25b are disposed in a manner sandwiching the observation lens 31a, on right and left sides as viewed toward the surface of FIG. 4. Moreover, on the distal end surface of the distal end cover 24, there are disposed the aperture portion 27 of the forward water-feeding channel at an upper right side of the observation lens 31a; the air/water feeding nozzle 60 on an upper left side; the observation lens 31b on a lower right side; and the aperture portion 26 of the treatment instrument channel on a lower left side, as viewed toward the surface of FIG. 4.

Note that locations of the observation lenses 31a, 31b, the aperture portions 26, 27, and the air/water feeding nozzle 60 disposed on the distal end cover 24 in the present embodiment will be described in detail later.

Figure 5:
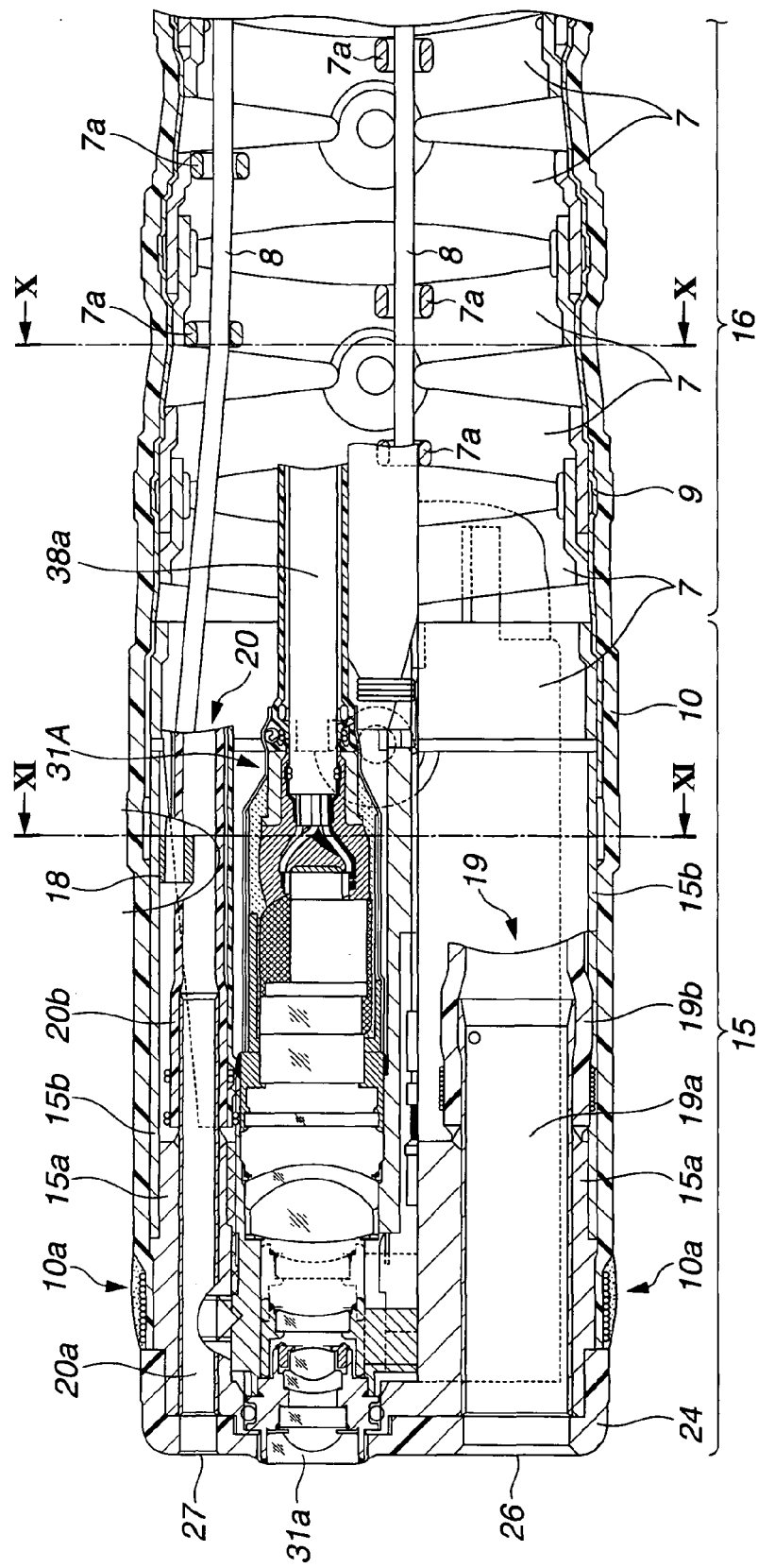
FIG. 5 is a section view of the distal end portion and a bending portion cut along V-V line of FIG. 4.
Figure 6:
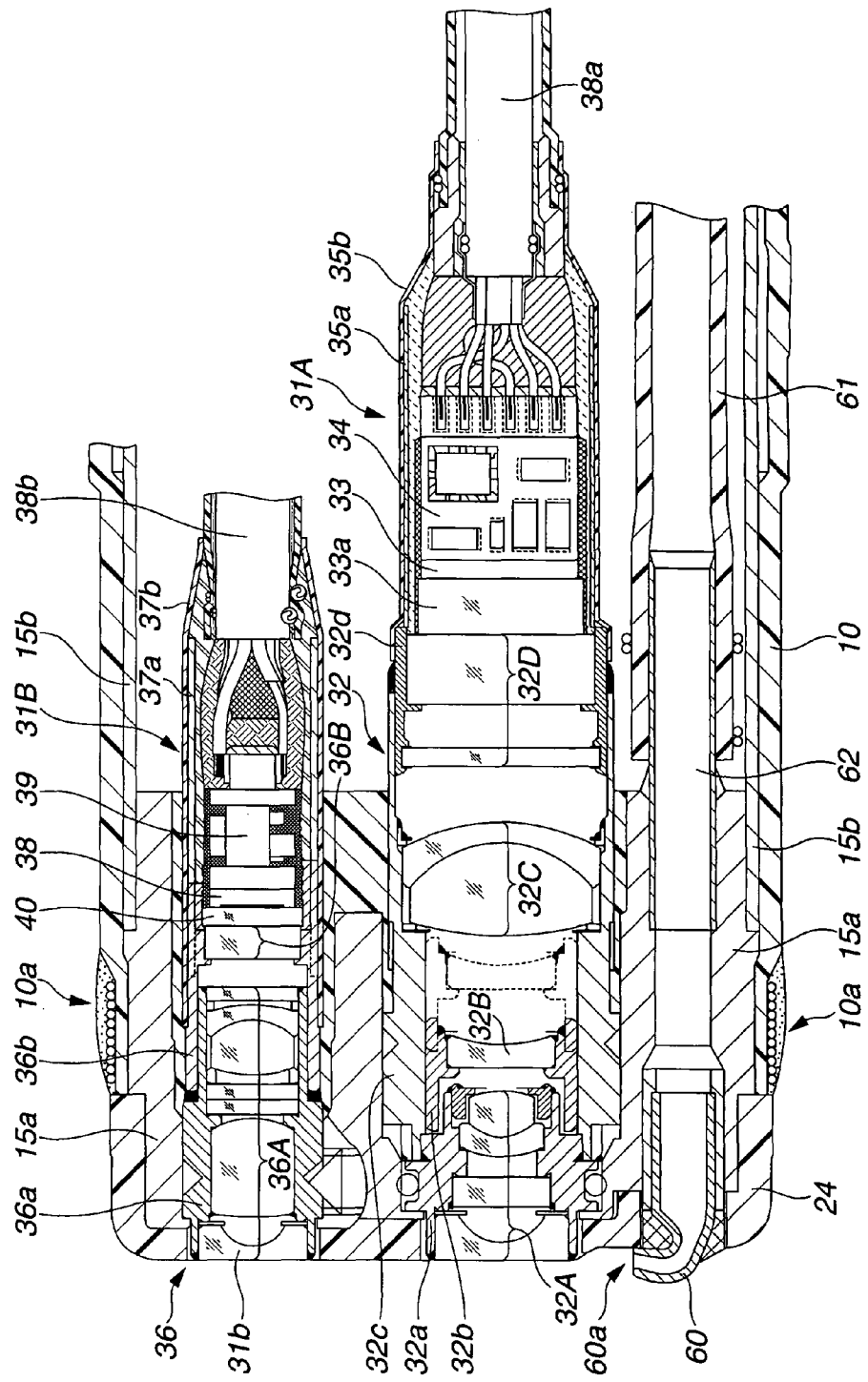
FIG. 6 is a section view of the distal end portion cut along VI-VI line of FIG. 4.
Figure 7:
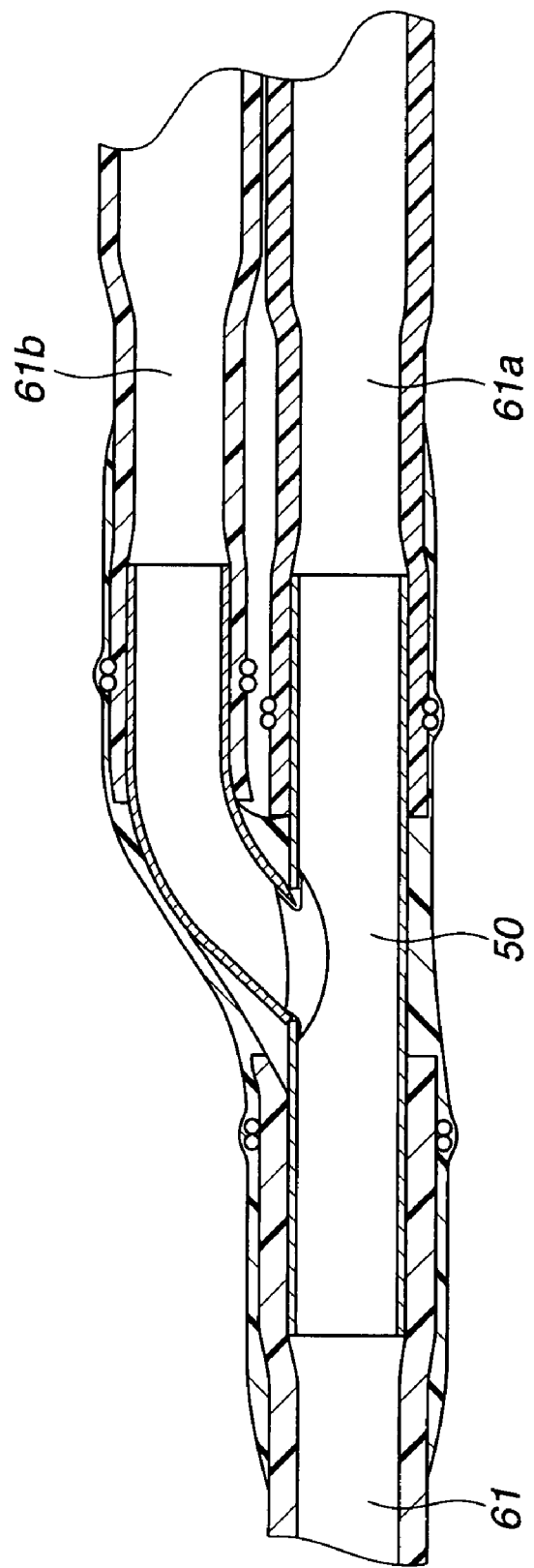
FIG. 7 is a section view showing a diverging part of an air/water feeding duct.
Figure 8:
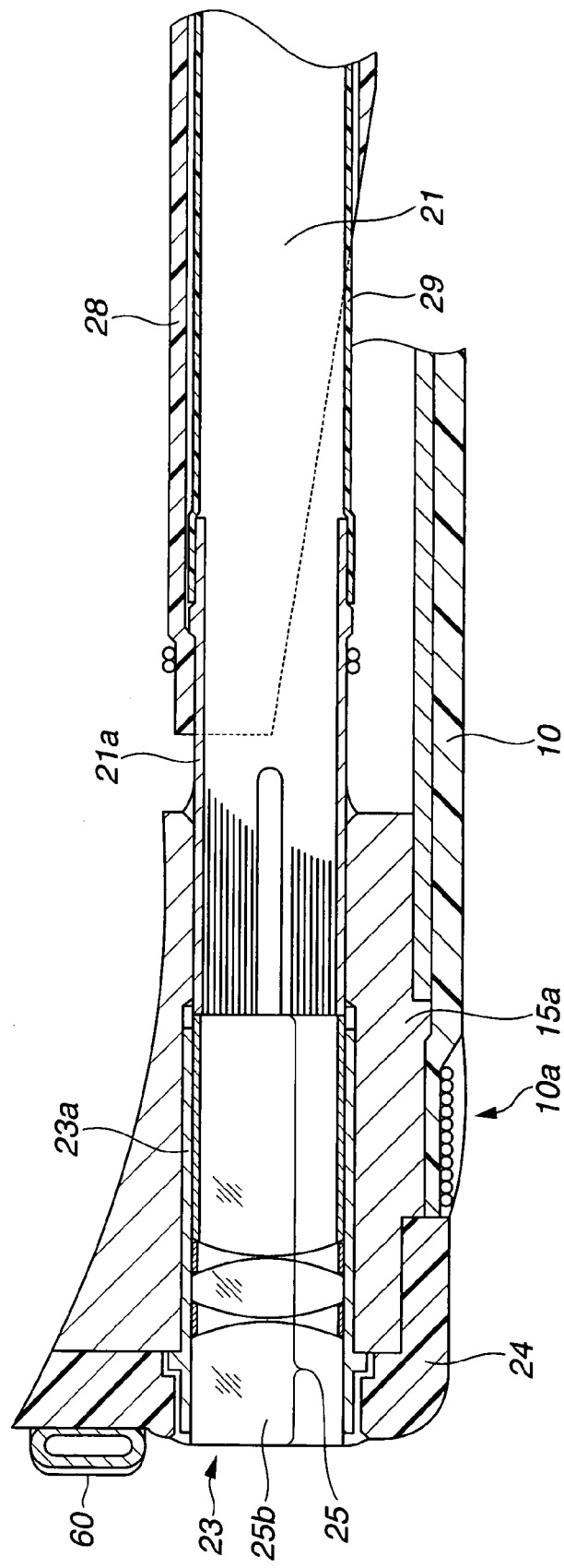
FIG. 8 is a section view of the distal end portion cut along VIII-VIII line of FIG. 4.
Figure 9:
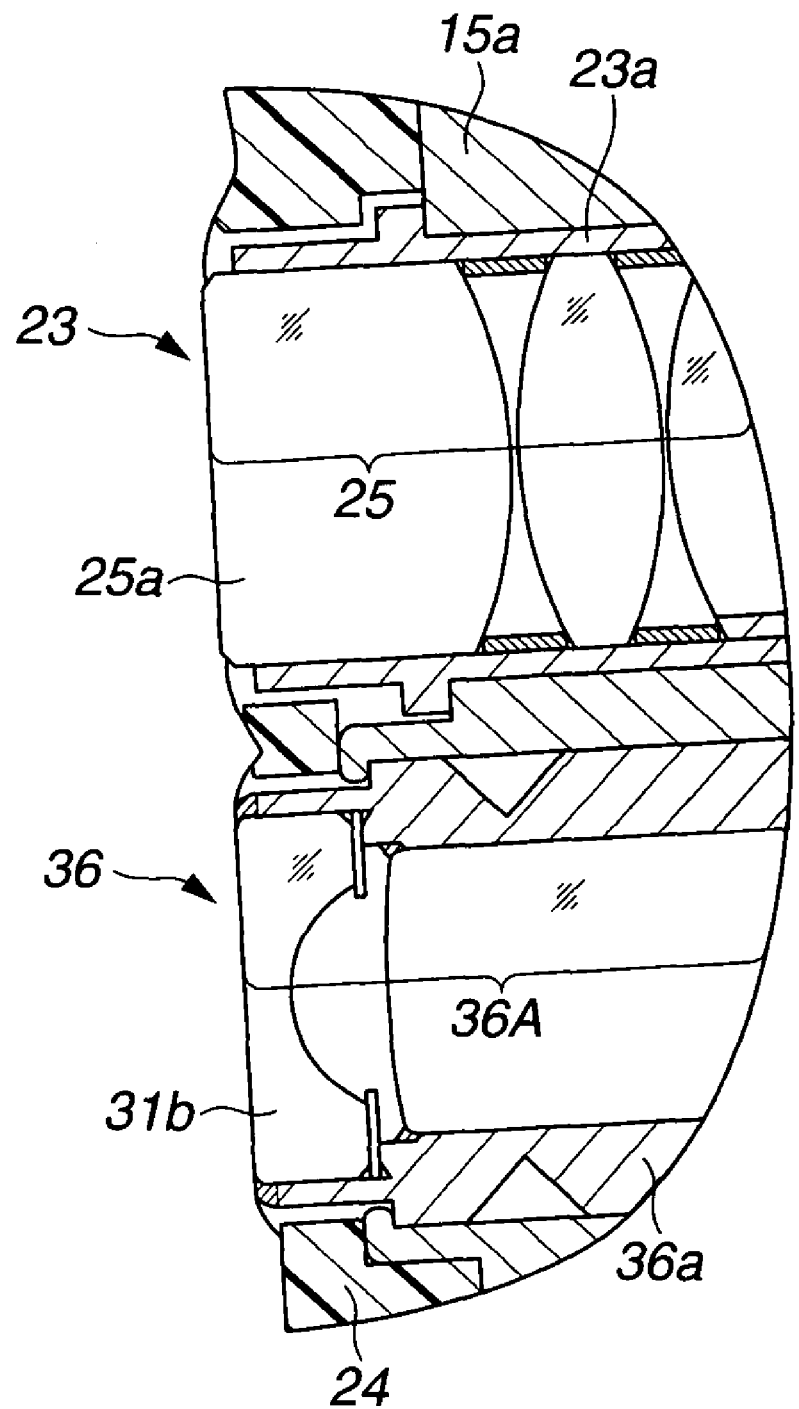
FIG. 9 is a section view of the distal end portion cut along IX-IX line of FIG. 4.
Figure 10:
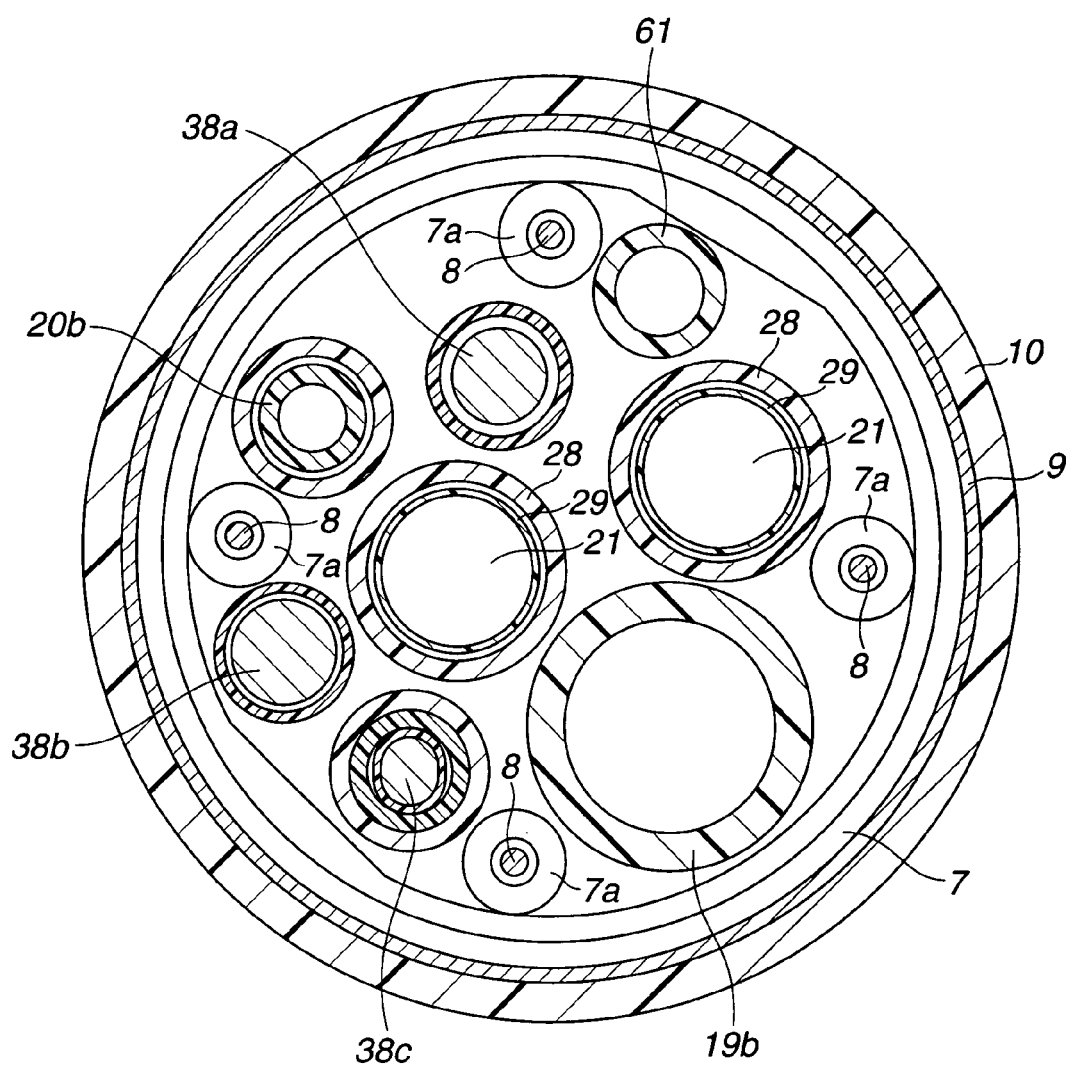
FIG. 10 is a section view of the distal end portion cut along X-X line of FIG. 5.
Figure 11:
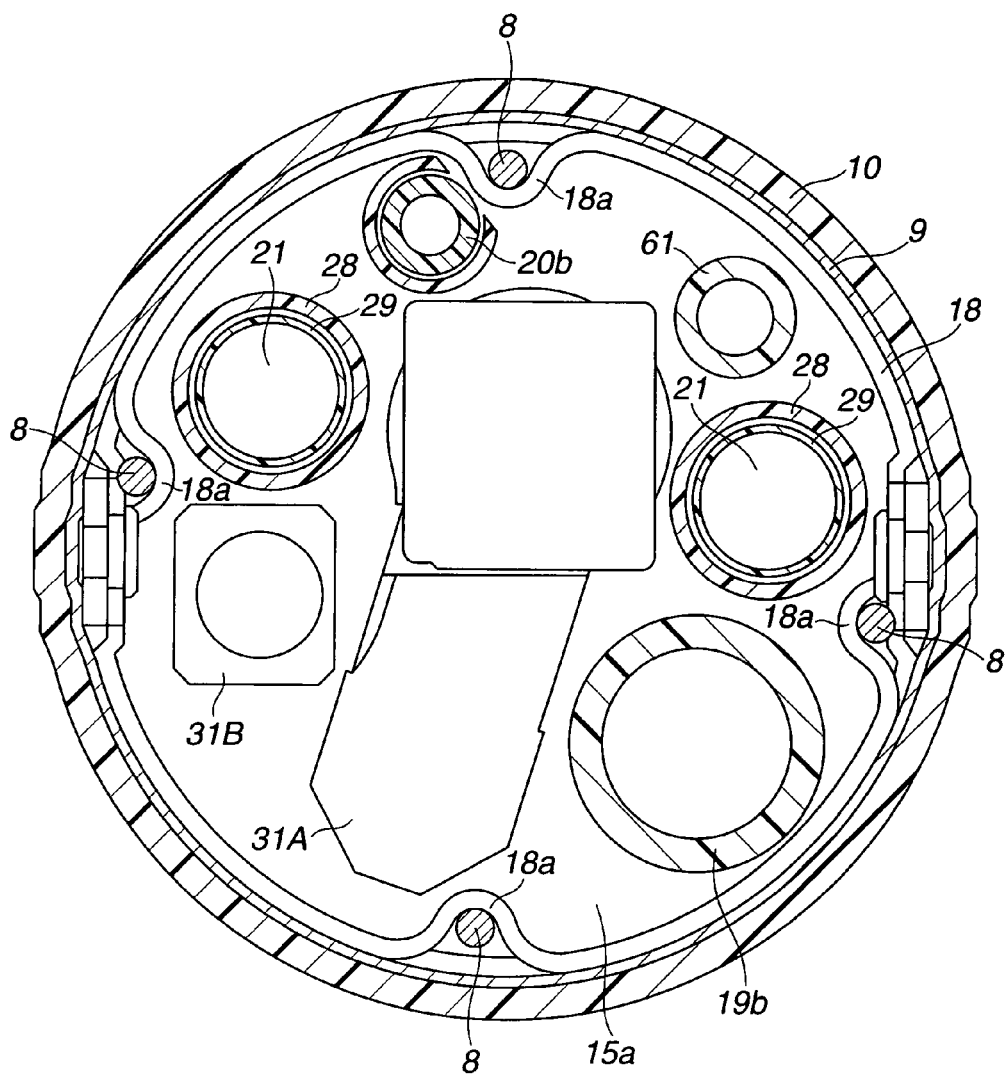
FIG. 11 is a section view of the bending portion cut along XI-XI line of FIG. 5.

Next, referring to FIGS. 5 to 11, internal configuration of the distal end part of the insertion portion 11 of the endoscope 2 of the present embodiment is described. Note that FIG. 5 is a section view of the distal end portion and the bending portion cut along V-V line of FIG. 4; FIG. 6 is a section view of the distal end portion cut along VI-VI line of FIG. 4; FIG. 7 is a section view showing a diverging part of the air/water feeding duct; FIG. 8 is a partial section view of the distal end portion cut along VIII-VIII line of FIG. 4; FIG. 9 is a partial section view of the distal end portion cut along IX-IX line of FIG. 4; FIG. 10 is a section view of the distal end portion cut along X-X line of FIG. 5; and FIG. 11 is a section view of the bending portion cut along XI-XI line of FIG. 5.

As shown in FIG. 5, in the bending portion 16 of the endoscope 2, a plurality of circular ring-shaped bending pieces 7 are rotatably provided in a linked manner. The bending pieces 7 each include on an inner circumferential surface four wire guards 7a fixedly provided thereon by means such as welding. The four wire guards 7a are fixed on an inner circumferential surface of one bending piece 7 at positions shifted by about 90 degrees from each other about the insertion axis (see FIG. 10).

The plurality of bending pieces 7 are coated, in a manner covering outer circumferences thereof, with a bending braid 9 made of a thin wire knitted in a pipe shape. The bending braid 9 is watertightly covered by an outer covering 10, thereby forming the bending portion 16.

The outer covering 10 provides a covering such that the insertion portion 11 including the distal end portion 15, the bending portion 16, and the flexible tube portion 17 forms one body over the entire length. An outer peripheral distal end part of the outer covering 10 is fixedly adhered with a spool adhering portion 10a in the distal end portion 15.

Also, in the insertion portion 11, four bending operation wires 8 are inserted which are bending operation means extending from the bending portion 16 toward a proximal end thereof. Distal end parts of these four bending operation wires 8 are respectively held and fixed, shifted by about 90 degrees from each other about the insertion axis, by four fixing portions 18a (see FIG. 11, only one is shown in FIG. 5) of a fixing ring 18 provided in the distal end portion 15. Proximal end side parts of the bending operation wires 8 are insertingly provided in the respective wire guards 7a provided to the bending pieces 7.

Note that the distal end portion 15 and each of the bending pieces 7 are connected in a linked manner such that the bending operation wires 8 held and fixed by the respective fixing portions 18a of the fixing ring 18 provided in the distal end portion 15 and inserted into the respective wire guards 7a of the bending pieces 7 are in a generally straight line, in a state where the insertion axis of the bending portion 16 is in a generally straight line.

Also, the proximal end portions of the bending operation wires 8 are connected to a bending operation mechanism not shown provided in the operation portion 12 (see FIG. 1) and connected to the bending operation knob, so as to be alternately pulled or relaxed.

By the four bending operation wires 8 each being pulled or relaxed through a predetermined operation of the bending operation knob, the bending portion 16 is operated to be bent in four directions. These four directions are up/down and left/right four directions of an endoscope image photographed by each of the image pickup units 31A, 31B and displayed on the monitor 5 as discussed below.

Also, two of the bending operation wires 8 as a first bending operation member configuring a first bending operation means for operating the bending portion 16 in up/down direction, and the other two of the bending operation wires 8 as a second bending operation member configuring a second bending operation means for operating the bending portion 16 in the left/right direction, respectively make pairs. That is, the two bending operation wires 8 respectively inserted and held in the two wire guards 7a in a direction corresponding to the up/down direction of the bending pieces 7 in the bending portion 16 are the first bending operation member. The other two bending operation wires 8 respectively inserted and held in the two wire guards 7a in the directions corresponding to the left/right direction in the bending pieces 7 in the bending portion 16 are the second bending operation member.

In the distal end portion 15, there are disposed a columnar member 5a made of a rigid metal and formed with a plurality of, seven in the present embodiment, hole portions; and a circular ring-shaped reinforcing ring 15b fitted onto a proximal end side outer circumference portion of the columnar member 15a. The fixing ring 18 including the above-described four fixing portions 18a is inserted and fitted on an inner circumferential side of the reinforcing ring 15b of the distal end portion 15. Further, a proximal end part of the reinforcing ring 15b is connected to a distal-most bending piece 7.

Two of the seven hole portions formed on the columnar member 15a of the distal end portion 15 form distal end parts of the treatment instrument channel 19 and the forward water-feeding channel 20. In the five remaining hole portions are respectively disposed the above-described normal light image pickup unit 31A, the fluorescent light image pickup unit 31B, the air/water feeding nozzle 60, and two illumination lens units described below.

The treatment instrument channel 19 includes the aperture portion 26 having an aperture on the distal end cover 24 provided on the distal end surface of the distal end portion 15; a generally cylindrical tube member 19a inserted and fitted in the hole portion of the columnar member 15a of the distal end portion 15; and a treatment instrument duct 19b made of a flexible tube, whose distal end part covers a proximal end portion of the tube member 19a and is connected and fixed to the proximal end portion with a spool.

The treatment instrument duct 19b is inserted in through the insertion portion 11, and has a proximal end with an aperture at the treatment instrument insertion port (not shown in FIG. 1) in the operation portion 12, as described above.

Also, the forward water-feeding channel 20 having the aperture portion 27 similarly on the distal end cover 24 includes a generally cylindrical tube member 20a inserted and fitted in the hole portion of the columnar member 15a of the distal end portion 15; and a forward water-feeding duct 20b covering the proximal end part of the tube member 20a and having a distal end part connected and fixed to the proximal end part with a spool.

The forward water-feeding duct 20b is inserted up to the connector 14 though the insertion portion 11, the operation portion 12, and the universal cable 13, and is connected to the forward water-feeding device 6a. Note that, as described above, the forward water-feeding duct 20b which is the forward water-feeding channel 20 is interposed with the forward water-feeding button (not shown) in operation portion 12.

As shown in FIG. 6, the air/water feeding nozzle 60 is a tubular member bent in a generally L shape, and has a proximal end part inserted and fitted in the hole portion of the columnar member 15a of the distal end portion 15 such that the spouting port 60a on the distal end side is oriented toward outer surface sides of the respective observation lenses 31a, 31b.

To a proximal end side of the hole portion of the columnar member 15a corresponding to the air/water feeding nozzle 60, a distal end part of the tube member 62 is inserted. A proximal end part of the tube members 62 is connected with the air/water feeding duct 61. Note that the tube member 62 and the air/water feeding duct 61 are connected and fixed by means of a spool.

As shown in FIG. 7, the air/water feeding duct 61 has a proximal end part connected to a diverging tube 50. The diverging tube 50 has divergence ends respectively connected to distal end parts of the air feeding duct 61a and the water feeding duct 61b. This brings the air/water feeding duct 61 into communication with the air feeding duct 61a and the water feeding duct 61b. Note that each of the ducts 61, 61a, 61b and the diverging tube 50 are connected and fixed by means of a spool. Respective connecting portions and the entire periphery of the diverging tube 50 are applied, for example, with an adhesive or the like, so that the each connecting portion is airtightly (watertightly) held.

Two of the seven hole portions formed on the columnar member 15a of the distal end portion 15 are each inserted and fitted with an illumination lens unit 23 from the distal end side. Proximal end parts of these two hole portions are respectively inserted with distal end parts of the light guide 21.

As shown in FIGS. 8 and 9, the illumination lens unit 23 includes a plurality of illumination lenses 25 and a holding barrel 23a for holding the illumination lenses 25. Note that the two illumination lens units 23 in the present embodiment respectively include the illumination lenses 25a, 25b present at the distal-most ends of the illumination lenses 25.

The light guide 21 has a distal end part covered with a cylindrical member 21a, and is coated with an outer covering 29 made of a plurality of strings of fibers bundled together. The cylindrical member 21a has a proximal end part connected and fixed to a tube 28 whose distal end part is fixed with a spool. The light guide 21 coated by the outer covering 29 passes in through the tube 28.

Note that one of the seven hole portions of the columnar member 15a is disposed with the normal light image pickup unit 31A, including the observation lens 31a, which is a first observation optical system fixed by a first observation optical system fixing member as first observation optical system fixing means such as a screw and adhesive, for example. This hole portion configures a first observation optical system disposition portion which is a first observation optical system disposition means.

Another one of the hole portions is disposed with the fluorescent light observation unit 31B, including the observation lens 31b, which is a second observation optical system fixed by a second observation optical system fixing member as second observation optical system fixing means, such as a screw and adhesive, for example. This hole portion configures a second observation optical system disposition portion which is a second observation optical system disposition means.

Further, in other two hole portions, the two illumination lens units, respectively including the illumination lenses 25, which are first and second illumination optical systems are respectively fixed and located by first and second illumination optical system fixing means such as a screw and adhesive, for example. Of these two hole portions, one configures a first illumination optical disposition portion as a first illumination optical disposition means, and the other configures a second illumination optical disposition portion as a second illumination optical disposition means.

Also, of the seven hole portions, a hole portion in which the air/water feeding portion is located configures an air/water feeding portion disposition portion as air/water feeding portion disposition means in which is fixed and located the air/water feeding nozzle 60 by a first air/water feeding portion fixing portion such as a screw and adhesive, for example.

Further, of the seven hole portions, a hole portion in which the treatment instrument channel 19 which is a first endoscope duct is located configures a first endoscope duct disposition portion as first endoscope duct disposition means.

Also, a hole portion in which the forward water-feeding channel 20 as a second endoscope duct is located configures a second endoscope duct disposition portion as second endoscope duct disposition means. The treatment instrument channel 19 is fixed and located in one of the seven hole portions by a first endoscope duct fixing member as first endoscope duct fixing means such as a screw and an adhesive, for example. The forward water-feeding channel 20 is fixed and located in one another hole portion by a second endoscope duct fixing member as second endoscope duct fixing means such as a screw and adhesive, for example.

Returning to FIG. 6, the normal light image pickup unit 31A includes a lens unit 32, an image pickup device 33 such as CCD (Charge Coupled Device) and CMOS (Complementary Metal-Oxide Semiconductor), and a circuit board 34.

The lens unit 32 includes first to fourth lens groups 32A to 32D, and first to fourth lens barrels 32a to 32d. In the present embodiment, the first lens group 32A formed by four object lenses containing the observation lens 31a is held by the first lens barrel 32a. The second lens 32B formed by one object lens is held by the second lens barrel 32b. Further, the third lens group 32C formed by two object lenses is held by the third lens barrel 32c. Still further, the fourth lens group 32D formed by three object lenses is held by the fourth lens barrel 32d.

Incidentally, the second lens barrel 32b for holding the second lens 32B is a moving barrel which can advance and retreat in a photographing optical axis direction for zooming. Note that the second lens barrel 32b is moved to advance and retreat in the photographing optical axis direction by a driving portion serving as driving means such as, for example, a motor and actuator not shown provided to the normal light image pickup unit 31A when a zooming operation lever not shown provided to the operation portion 12 is operated by a user.

The driving portion for moving the second lens barrel 32b to advance and retreat in the photographing optical axis direction is supplied with a drive-stop signal through a signal line 38c shown in FIG. 10. The signal line 38c is inserted from the normal light image pickup unit 31A up to the operation portion 12 in through the insertion portion 11:

The image pickup device 33 is provided, on a light receiving surface side, with a cover lens 33a adjacently provided on a proximal end side of an object lens at the proximal-most end of the fourth lens barrel 32d, and outputs an electrical signal corresponding to an optical image to the circuit board 34. The circuit board 34 includes electrical parts and a wiring pattern, photoelectrically converts an optical image from the image pickup device 33 to an electric image signal, and then outputs the image signal to the signal cable 38a. Note that the circuit board 34 is connected with a plurality of signal lines of the signal cable 38a by means of soldering or the like.

The cover lens 33a, the image pickup device 33, the circuit board 34, and a distal end part of the signal cable 38a have respective outer circumference portions unitedly covered by an insulation sealing resin or the like, and are coated by a reinforcing circular ring portion 35a and an insulating tube 35b.

The signal cable 38a transmits image signals acquired by the image pickup device 33 and the circuit board 34 of the normal light image pickup unit 31A to the signal processing circuit 46 of the processor 4 via the relay board 42 and the signal cable 43 of the connector 14 shown in FIG. 1.

Meanwhile, like the normal light image pickup unit 31A, the fluorescent light image pickup unit 31B includes a lens unit 36, an image pickup device 38 such as CCD and CMOS, and a circuit board 39.

The lens unit 36 includes first and second lens groups 36A, 36B and first and second lens barrels 32a, 32b. In the present embodiment, the first lens group 36A formed by seven object lenses including the observation lens 31b is held by the first lens barrel 36a, and the second optical lens 36B is held by the second lens barrel 36b.

The image pickup device 38 is provided, on a light receiving surface side, with a cover lens 40 adjacently provided on a proximal end side of an object lens at the proximal-most end of the second lens barrel 36*b*. The image pickup device 38 outputs an electrical signal of an optical image to the circuit board 39.

The circuit board 39 includes electrical parts and a wiring pattern, like the circuit board 34 of the normal light image pickup unit 31A. The circuit board 39 is connected with a plurality of signal lines of the signal cable 38*a* by means of soldering or the like. The circuit board 39 photoelectrically converts an optical image from the image pickup device 38 to an electric image signal, and then outputs the image signal to the signal cable 38*b*.

The cover lens 40, the image pickup device 33, the circuit board 34, and a distal end part of the signal cable 38*a* have respective outer circumference portions unitedly covered by an insulation sealing resin or the like, and are coated by a reinforcing circular ring portion 35*a* and the insulating tube 35*b*.

The signal cable 38*b* transmits image signals acquired by the image pickup device 38 and the circuit board 39 of the fluorescent light image pickup unit 31B to the signal processing circuit 46 of the processor 4 via the relay board 42 and the signal cable 43 of the connector 14 shown in FIG. 1.

The above-described normal light image pickup unit 31A and the fluorescent light image pickup unit 31B are respectively inserted into predetermined hole portions provided to the columnar member 15*a* of the distal end portion 15, and are firmly fixed thereto with a fixing member such as a screw along with an adhesive or the like.

In the present embodiment, the observation lens 31*a* provided at the distal end of the normal light image pickup unit 31A has a lens diameter (caliber as outer diameter) that is larger than a lens diameter of the observation lens 31*b* located at the distal end of the fluorescent light image pickup unit 31B.

Also, setting directions of the image pickup units 31A, 31B in the distal end portion 15 are determined such that respective light receiving surfaces of the two image pickup devices 33, 38 are orthogonal to the insertion axis of the insertion portion 11, and horizontal transfer directions and vertical transfer directions of the two image pickup devices 33, 38 agree to each other, respectively.

Further, subject images photographed by the image pickup units 31A, 31B are displayed on the monitor 5 (see FIG. 1). Note that up/down direction of the monitor 5 agrees with vertical transfer direction of the CCD or CMOS device of each of the image pickup devices 33, 38, and left/right direction of the monitor 5 agrees with horizontal transfer direction of the CCD or CMOS device of each of the image pickup devices 33, 38. In other words, up/down and left/right directions of an endoscope image photographed by each of the image pickup units 31A, 31B agree with up/down and left/right directions of the monitor 5.

Up/down and left/right directions of the bending portion 16 of the insertion portion 11 are determined to correspond to the up/down and left/right directions of an endoscope image displayed on the monitor 5. That is, the four bending operation wires 8 inserted in through the bending portion 16 are pulled and relaxed by a predetermined operation of the bending operation knob provided to the operation portion 12 as described above, so as to render the bending portion 16 bendable in up/down and left/right four directions corresponding to the up/down and left/right directions of an image displayed on the monitor 5.

In other words, setting directions of the image pickup units 31A, 31B in the distal end portion 15 are determined such that horizontal transfer directions and vertical transfer directions of the image pickup devices 33, 38 respectively agree so that up/down and left/right directions of an endoscope image displayed on the monitor 5 always agree with those directions of the bending operation directions of the bending portion 16 even when normal light observation and fluorescent light observation are switched from one to the other.

Thus, the user can perform bending operation of the bending portion 16 in up/down and left/right directions without having a sense of incongruity about those directions of an endoscope image displayed on the monitor 5 when endoscope images with normal light and fluorescent light are switched from one to the other.

Note that, in the description below, up/down direction as a first direction will be described as up/down direction of an endoscope image displayed on the monitor 5 and up/down direction in which the bending portion 16 is operated to be bent. Normally, the monitor 5 is installed such that up/down direction thereof generally agrees with plumb up/down direction. Further, left/right direction as a second direction which is generally orthogonal to the up/down direction is identical to the left/right direction of an endoscope image displayed on the monitor 5 and the left/right direction in which the bending portion 16 is operated to be bent.

Here, actions of the above-described endoscope system 1 are described.

As shown in FIG. 1, a user connects the connector 14 of the endoscope 2 to the light source device 3, and further connects one end of the scope cable 44 to the connector 14 and the other end of the scope cable 44 to the processor 4. The user also connects the air feeding duct 61*a* and the water feeding duct 61*b* to the air/water feeding device 6.

Then, the user turns on power switches of the light source device 3 and the like to bring these devices into operation state. At this time, the respective control circuits 47, 58 of the processor 4 and the light source device 3 are rendered capable of transmitting and receiving control signals.

The relay board 42 is set to select the normal light image pickup unit 31A side in activation state. Also, the control circuit 47 performs a control operation so that a normal light observation state is set. That is, the control circuit 47 sends a control signal to the control circuit 58 of the light source device 3, to make a setting to obtain a state of supplying illumination light for normal light observation.

Further, the control circuit 47 controls to drive the driving circuit 45*a* and sets operation state of the signal processing circuit 46 to normal light observation mode.

The user inserts the insertion portion 11 of the endoscope 2 in the body cavity, to make a setting so that a diseased part of the diagnosis object can be observed.

The light source device 3 is brought into a state of supplying illumination light for normal light observation as described above. In this state, the rotary filter 53 is rotationally driven by the motor 55, with the RGB filter located in an illumination optical path. Then, RGB illumination lights are supplied to the light guide 21 in a surface sequential manner. Synchronously therewith, the driving circuit 45*a* outputs a driving signal to illuminate a diseased part or the like in the body cavity of the patient through the illumination lenses 25*a*, 25*b*.

The illuminated subject such as a diseased part is focused on a light receiving surface of the image pickup device 33 through the lens unit 32 of the normal light image pickup unit 31A, and is subject to photoelectric conversion. Then, the image pickup device 33, when applied with a driving signal, outputs photoelectrically converted signals. The signals are inputted to the signal processing circuit 46 via the signal cable 38*a* and the common signal cable 43 selected by the relay board 42.

The signals inputted to the signal processing circuit 46 are subject to A/D conversion therein, and thereafter temporarily stored in an RGB memory.

Subsequently, the signals stored in the RGB memory are simultaneously read out into synchronized R, G, B signals, which are further D/A converted into analog R, G, B signals to be color displayed on the monitor 5.

If the user desires to inspect the diseased part in more detail by fluorescent light observation in addition to normal light observation, the user turns on the control switch 48a. Then, on receiving the switching instruction signal, the control circuit 47 performs switching control of the relay board 42, and sets the light source device 3 to a state of supplying excitation light for fluorescent light observation via the control circuit 58.

The control circuit 47 also controls the driving circuit 45b into operation state, and sets the signal processing circuit 46 to a processing mode for fluorescent light observation.

In this case, the control circuit 58 in the light source device 3 causes the gear-equipped motor 57 to move the rotary filter 53 along with the motor 5 in a direction orthogonal to an illumination optical path, so that the excitation light filter is located in the illumination optical path.

In this state, light from the lamp 51 is transmitted by the excitation light filter in a wavelength band of about, for example, 400 to 450 nm, to be supplied to the light guide 21. The excitation light is then irradiated to a diseased part or the like in the body cavity, through the illumination lenses 25a, 25b.

When the diseased part or the like irradiated with the excitation light is an abnormal region such as of carcinoma tissues, the part absorbs the excitation light and emits fluorescent light stronger than in a case of a normal organization. The light of the region emitting the fluorescent light is focused on the light receiving surface of the image pickup device 38 through the lens unit 36 of the fluorescent light image pickup unit 31B, and then is subject to photoelectric conversion.

The image pickup device 38, when applied with a driving signal from the driving circuit 45b, outputs photoelectrically converted signals. In this case, the signals are amplified in the image pickup device 38 and then outputted therefrom. The signals are inputted to the signal processing circuit 46 through the signal cable 38b and the common signal cable 43 selected by the relay board 42.

The signals inputted into the signal processing circuit 46 are A/D converted therein, and then stored in the RGB memory, simultaneously, for example.

Thereafter, the signals stored in the RGB memory are simultaneously read out into synchronized R, G, B signals, which are further D/A converted into analog R, G, B signals to be displayed on the monitor 5 in a black and white manner.

Note that the signals inputted into the signal processing circuit 46 may be provided in pseudo colors and displayed by comparing the signals in level with a plurality of thresholds and changing colors to be assigned depending on the comparison result.

Thus, the present embodiment, which is capable of performing the normal light observation as well as the fluorescent light observation, can realize an endoscope facilitating diagnosis compared with an endoscope only for normal light observation. Moreover, the present embodiment, which is provided with the respective image pickup unit 31A, 31B, can obtain fine normal light observation images and special light observation images.

Specifically, when performing a fluorescent light image pickup in particular, it is necessary to capture light weaker than in normal observation: light preferably having a high signal to noise ratio. In this case, using a normal image pickup device for both observations easily results in an image having low signal to noise ratio. However, the present embodiment can obtain a fluorescent light image with a good signal to noise ratio by adopting the image pickup device 38 suitable for fluorescent light image pickup, which is more sensitive to light relative to the image pickup device 33 for normal observation.

Further, provided with the switching relay board 42 to connect only one of the two image pickup units 31A, 31B to the processor 4, the endoscope system 1 can be formed to be more compact than when the two image pickup unit 31A, 31B each always has to be driven and signal processed.

Still further, the present embodiment can reduce diameter of the insertion portion 11, relieve pain given to a patient in insertion, and expand the insertable application area, because the single air/water feeding nozzle 60 is used to spray gas or liquid onto the outer surfaces of the both observation lenses 31a, 31b to set the surfaces to a clean state to allow securing good observation field of view.

Yet still further, the endoscope 2 of the present embodiment, having an similar exterior structure to that of an existing endoscope only including an image pickup unit for normal light observation, can also be used as an endoscope for normal light observation in a similar manner with an existing endoscope by connecting the endoscope 2 via the scope cable 44 to a processor not shown for driving and signal processing an existing endoscope only including an image pickup unit for normal light observation. In other words, the endoscope 2 can also be used connected to an existing processor, while maintaining compatibility similar to that for the existing endoscope only including the image pickup unit for normal light observation.

Here, the endoscope 2 of the present embodiment has various characteristics (effects) owing to structures described below.

Figure 12:
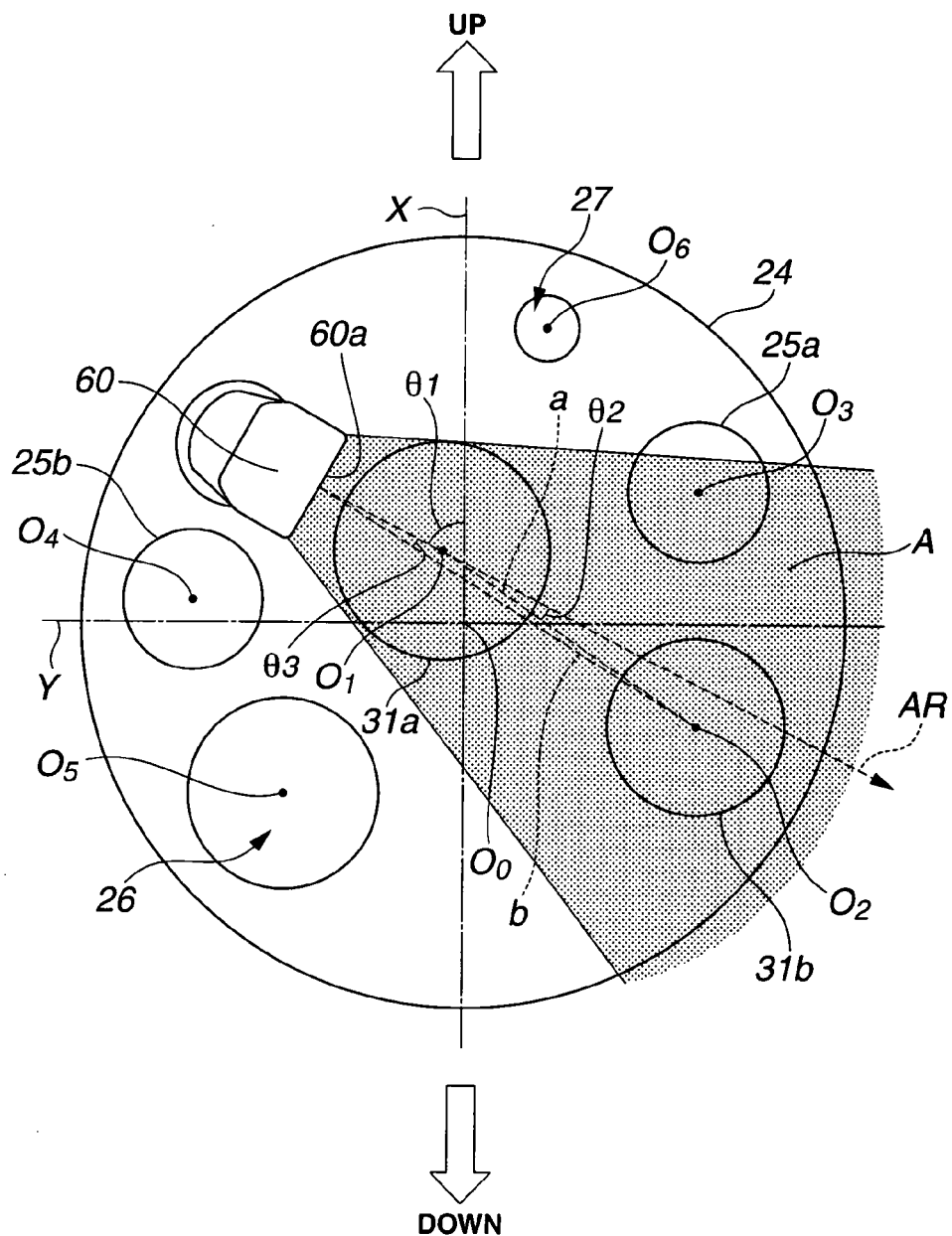
FIG. 12 is a plan view of the distal end cover as viewed from the front.

First, referring to FIG. 12, there are described in detail, dispositions of the air/water feeding nozzle 60 and each of the observation lenses 31a, 31b disposed on the distal end cover 24.

FIG. 12 is a front view showing a distal end surface of the distal end cover. Note that, in the following description, center of the distal end cover 24 is denominated as $O_0$, center of the observation lens 31a of the normal light image pickup unit 31A as $O_1$ and center of the observation lens 31b of the fluorescent light image pickup unit 31B as $O_2$. Also, centers of the two illumination lenses 25a, 25b described below are respectively denominated as $O_3$, $O_4$, center of the aperture portion 26 of the treatment instrument channel 19 as $O_5$, and center of the aperture portion 27 of the forward water-feeding channel 20 as $O_6$. Further, a line passing through the center $O_0$ of the distal end surface of the distal end cover 24 and oriented in a bending up/down direction of the bending portion 16 is denominated as a perpendicular line X, and a line in a bending left/right direction as a horizontal line Y. Note that, in the following description, the perpendicular line X in the present embodiment is regarded as a line equated with a plumb line.

As described above, the air/water feeding nozzle 60 is disposed on the upper left side on the distal end surface of the distal end cover 24 as viewed toward the surface of FIG. 12, such that the spouting port 60a of the air/water feeding nozzle 60 faces the observation lens 31a. Note that, the air/water feeding nozzle 60 may also be disposed on the upper right side on the distal end surface of the distal end cover 24 as viewed toward the surface of FIG. 12, such that the spouting port 60a of the air/water feeding nozzle 60 faces the observation lens 31a. At this time, the air/water feeding nozzle 60 and each of the observation lenses 31a, 31b are located on the distal end surface of the distal end cover 24 so as to line up on a generally straight line.

In the present embodiment, the air/water feeding nozzle 60 is disposed on the distal end surface of the distal end cover 24 such that gas or liquid such as distilled water or air is spouted out from the spouting port 60a of the air/water feeding nozzle 60 in the direction of an arrow line AR in the drawing. The air/water feeding nozzle 60 spouts out, in a spreading manner, the gas or liquid such as distilled water or air into a gas/liquid spouting area A from the spouting port 60a. Note that the arrow line AR is a line in a direction generally orthogonal to the distal end surface of the air/water feeding nozzle 60 including the spouting port 60a, and passing through the center of a hole surface of the spouting port 60a.

Setting direction of the air/water feeding nozzle 60 about an axis thereof, that is, direction in which the spouting port 60a faces, is determined such that an observation optical axis passing through the center $O_1$ of the observation lens 31a intersects the above-described arrow line AR. In other words, the direction in which spouting port 60a of the air/water feeding nozzle 60 faces is determined such that the arrow line AR as the spouting direction of the gas or liquid such as distilled water or air is in a predetermined angle θ as a first angle with respect to the perpendicular line X.

On the other hand, the observation lens 31b of the fluorescent light image pickup unit 31B is disposed on a lower right side on the distal end surface of the distal end cover 24 toward the surface of FIG. 10, such that an outer surface of the observation lens 31b has a part intersecting at least the arrow line AR when the distal end cover 24 is viewed from a distal end thereof. The observation lens 31b is also disposed on the distal end surface of the distal end cover 24 such that the center $O_2$ of the observation lens 31b is located on a side lower than the line segment of the arrow line AR.

As described above, the air/water feeding nozzle 60 and the two observation lenses 31a, 31b are adjacently provided on the generally straight line on the distal end surface of the distal end cover 24.

In detail, a line a linking the center $O_1$ of the observation lens 31a of the normal light image pickup unit 31A and the center $O_2$ of the observation lens 31b of the fluorescent light image pickup unit 31B is slightly shifted toward a lower side when the distal end cover 24 is viewed from the distal end surface side thereof, with a predetermined angle θ2 with respect to the arrow line AR. In other words, a line b linking the center of a hole surface of the spouting port 60a of the air/water feeding nozzle 60 and the center $O_2$ of the observation lens 31b is slightly shifted toward a lower side when the distal end cover 24 is viewed from the distal end surface side, with a predetermined angle θ3 with respect to the arrow line AR.

This determines respective disposition positions of the observation lenses 31a, 31b on the distal end cover 24. In line with these positions, direction of the spouting port 60a of the air/water feeding nozzle 60 (direction of the arrow line AR) is determined. Further, the angles θ2, θ3 are set in ranges such that the gas/liquid spouting area A from the air/water feeding nozzle 60 includes the entire outer surface of the observation lens 31b.

Note that the gas/liquid spouting area A of the air/water feeding nozzle 60 is set to entirely include an outer surface of the observation lens 31a of the normal light image pickup unit 31A when viewed from the distal end side of the distal end cover 24.

Also, the observation lens 31a having a lens diameter (caliber as outer diameter) larger than an outer diameter of the observation lens 31b is disposed on the distal end surface of the distal end cover 24, close to the air/water feeding nozzle 60.

That is, the distal end cover 24 has the air/water feeding nozzle 60 at a position on an upper side than the horizontal line Y generally bisecting the bending up/down direction of the bending portion 16 with respect to a direction viewed from the distal end surface side, that is, up/down direction of the vertical transfer direction in which the respective image pickup devices 33, 38 included in the image pickup units 31A, 31B perform processings. In other words, the air/water feeding nozzle 60 is disposed on the distal end cover 24, apart from the horizontal line Y in an opposite direction from the spouting direction (arrow line AR direction).

Further, on the distal end cover 24, the air/water feeding nozzle 60 is disposed such that a section surface in a direction orthogonal to a longitudinally directed axis of the air/water feeding nozzle 60 (axis parallel to the insertion direction) does not exist on the perpendicular line X which bisects a left/right direction (which is reverse to the bending left/right direction of the bending portion 16) relative to the direction as viewed from the distal end surface side of the distal end cover, that is, left/right direction of the vertical transfer direction in which the image pickup devices 33, 38 included in the respective image pickup units 31A, 31B perform processings.

Note that, in the present embodiment, the air/water feeding nozzle 60 is disposed on a position on the distal end surface of the distal end cover 24, so as to be apart from the perpendicular line X in a left direction by a predetermined distance, when viewed from the distal end surface side of the distal end cover 24. That is, the air/water feeding nozzle 60 is located such that a longitudinal axis thereof is present at a position which is on an upper side than the horizontal line Y bisecting the distal end cover 24 into upper and lower sides and is shifted toward left side from the perpendicular line X bisecting the distal end cover 24 into right and left sides, when viewed from the distal end surface side of the distal end cover 24.

As a result of the foregoing, the endoscope 2 of the present embodiment can be secured of a good observation field of view by using the single air/water feeding nozzle 60 to spray gas or liquid onto the outer surfaces of the respective observation lenses 31a, 31b to set the surfaces in a clean state, when the air/water feeding nozzle 60, the observation lens 31a of the normal light image pickup unit 31A, and the observation lens 31b of the fluorescent light image pickup unit 31B provided on the distal end surface of the distal end cover 24 are located on a generally straight line.

Also, the longitudinal axis of the air/water feeding nozzle 60 is shifted toward an upper side than the horizontal line Y bisecting the distal end cover 24 to upper and lower sides, and by a predetermined distance from the perpendicular line X bisecting the distal end cover 24 to right and left sides. Therefore, when the insertion portion 11 is in a generally straight line, the air/water feeding duct 61 communicating with the air/water feeding nozzle 60 is generally straightly inserted in through the distal end portion 15 and the bending portion 16, without coming into contact with the four fixing portions 18a of the fixing ring 18 disposed in the distal end portion 15 and the four wire guards 7a respectively provided on the bending pieces 7 disposed in the bending portion 16.

Further, because the above-described disposition of the air/water feeding nozzle 60 prevents the air/water feeding duct 61 from coming into contact in the bending portion 16 with the four bending operation wires 8 respectively inserted and held in the four wire guards 7a of each of the bending pieces 7, movement of the bending operation wire 8 due to pulling and relaxing is not obstructed, and deterioration of the bending operation wire 8 due to scratch can be prevented.

As a result of the foregoing, the endoscope 2 of the present embodiment can reduce the diameter of the insertion portion 11, particularly of the distal end portion 15 and the bending portion 16, relieve pain given to a patient in insertion, and expand the insertable application area in the body cavity.

In addition, the endoscope 2 is generally used with the bending up/down direction of the bending portion 16 being adjusted to up/down direction of the plumb direction by the user. Therefore, liquid such as distilled water spouted out from the spouting port 60*a* of the air/water feeding nozzle 60 flows toward a lower side, on a side farther from the spouting port 60*a*, due to the effect of gravity.

Further, in a case where gas or liquid such as distilled water or air is spouted out from the spouting port 60*a* of the air/water feeding nozzle 60, and at the same time suction is performed through the treatment instrument channel 19, the liquid or gas is applied with a drawing force toward the aperture portion 26 due to the suction force from the aperture portion 26 of the treatment instrument channel 19 provided on a lower side on distal end cover 24, and is thereby changed in flow direction toward the bending lower side.

Under such circumstances, in the endoscope 2 of the present embodiment, the observation lens 31*b* of the fluorescent light image pickup unit 31B is located on the distal end surface of the distal end cover 24 such that the line a linking the center $O_2$ thereof with the center $O_1$ of the observation lens 31*a* of the normal light image pickup unit 31A is shifted by a predetermined angle θ2 toward the bending lower side of the bending portion 16 with respect to the arrow line AR which is the spouting direction of a liquid such as distilled water spouted out from the spouting port 60*a* of the air/water feeding nozzle 60.

Accordingly, on the distal end surface of the distal end cover 24, the observation lens 31*b* positioned farther than the observation lens 31*a* from the air/water feeding nozzle 60 is efficiently sprayed with a liquid such as distilled water flowing down toward the bending lower side than the spouting direction due to the effect of gravity. The observation lens 31*b* is thus cleaned into a clean state and secured of a good observation field of view. Further, the observation lens 31*b* is likewise efficiently sprayed with gas or liquid such as distilled water or air whose flow is changed to the bending lower side by suction performed, to be cleaned into a clean state and secured of a good observation field of view.

Furthermore, the endoscope 2 inserted in the body cavity of the patient has the insertion portion 11 adhered with filth or the like. Incidentally, the distal end surface of the distal end cover 24 is generally perpendicular to the insertion direction and is therefore easily adhered with filth or the like. In particular, the observation lens 31*a* of the normal light image pickup unit 31A and the observation lens 31*b* of the fluorescent light image pickup unit 31B are required to be surely cleaned of adhering filth or the like in order to secure respective observation fields of view.

In particular, the endoscope 2 is required to secure better observation field of view for the normal light observation than for the fluorescent light observation in which tone of tissue pigments are observed, because normal light is more frequently used than the fluorescent light observation to observe a patient's body cavity. That is, it is preferable that the endoscope has larger amount of light for photographing in normal light observation. To this end, the normal light image pickup unit 31A is disposed in the vicinity of the generally center of the distal end surface of the distal end portion 15, so as to take in light for picking up an image from the observation lens 31*a* having a larger lens diameter (caliber as outer diameter) than that of the observation lens 31*b* for leading incident light for picking up an image to the fluorescent light image capturing unit 31B.

Also, gas or liquid such as distilled water or air spouted out from the spouting port 60*a* of the air/water feeding nozzle 60 has larger spouting force on the side closer to the spouting port 60*a*. On a farther side in the spouting direction, the spouting force decreases and density of the gas or liquid also decreases due to spreading thereof.

Under such circumstances, in the endoscope 2 of the present embodiment, the observation lens 31*a* of the normal light image pickup unit 31A having a larger lens diameter (caliber as outer diameter) than that of the observation lens 31*b* of the fluorescent light image capturing unit 31B is disposed at a position closer to the air/water feeding nozzle 60 on the distal end surface of the distal end cover 24, as shown in FIG. 11. As described above, the entire outer surface of the observation lens 31*a* is included in the spouting area A of the gas or liquid such as distilled water or air spouted out from the spouting port 60*a* of the air/water feeding nozzle 60.

Thus, in the endoscope 2, the observation lens 31*a* having a larger lens diameter (caliber as outer diameter) easily adhered with body fluid, filth or the like is closer to the air/water feeding nozzle 60, and accordingly, cleanability of the observation lens 31*a* can be improved without being affected by decrease of spouting force and density of gas or liquid such as distilled water or air spouted out from the spouting port 60*a*.

Note that as described above, the air/water feeding nozzle 60, the observation lens 31*a* of the normal light image pickup unit 31A, and the observation lens 31*b* of the fluorescent light image pickup unit 31B are adjacently provided on a generally straight line on the distal end surface of the distal end cover 24 shown in FIG. 12, in the endoscope 2 of the present embodiment. Further, on the arrow line AR which is the spouting direction of gas or liquid such as distilled water or air to be spouted out from the spouting port 60*a* of the air/water feeding nozzle 60, other components are not disposed on the distal end surface of the distal end cover 24.

That is, on the arrow line AR, other components are not disposed on an outer circumferential side on the distal end surface of the distal end cover 24 from the observation lens 31*b* of the fluorescent light image pickup unit 31B.

With such a configuration, the gas or liquid that cleaned the filth adhering on each of the observation lenses 31*a*, 31*b* flows toward an outer edge portion of the distal end cover 24 in the arrow line AR direction which is the spouting direction, without flowing to the other components. As a result, when the gas or liquid such as distilled water or air is spouted out from the air/water feeding nozzle 60, the distal end surface of the distal end cover 24 of the endoscope 2 is surely cleaned.

Figure 13:
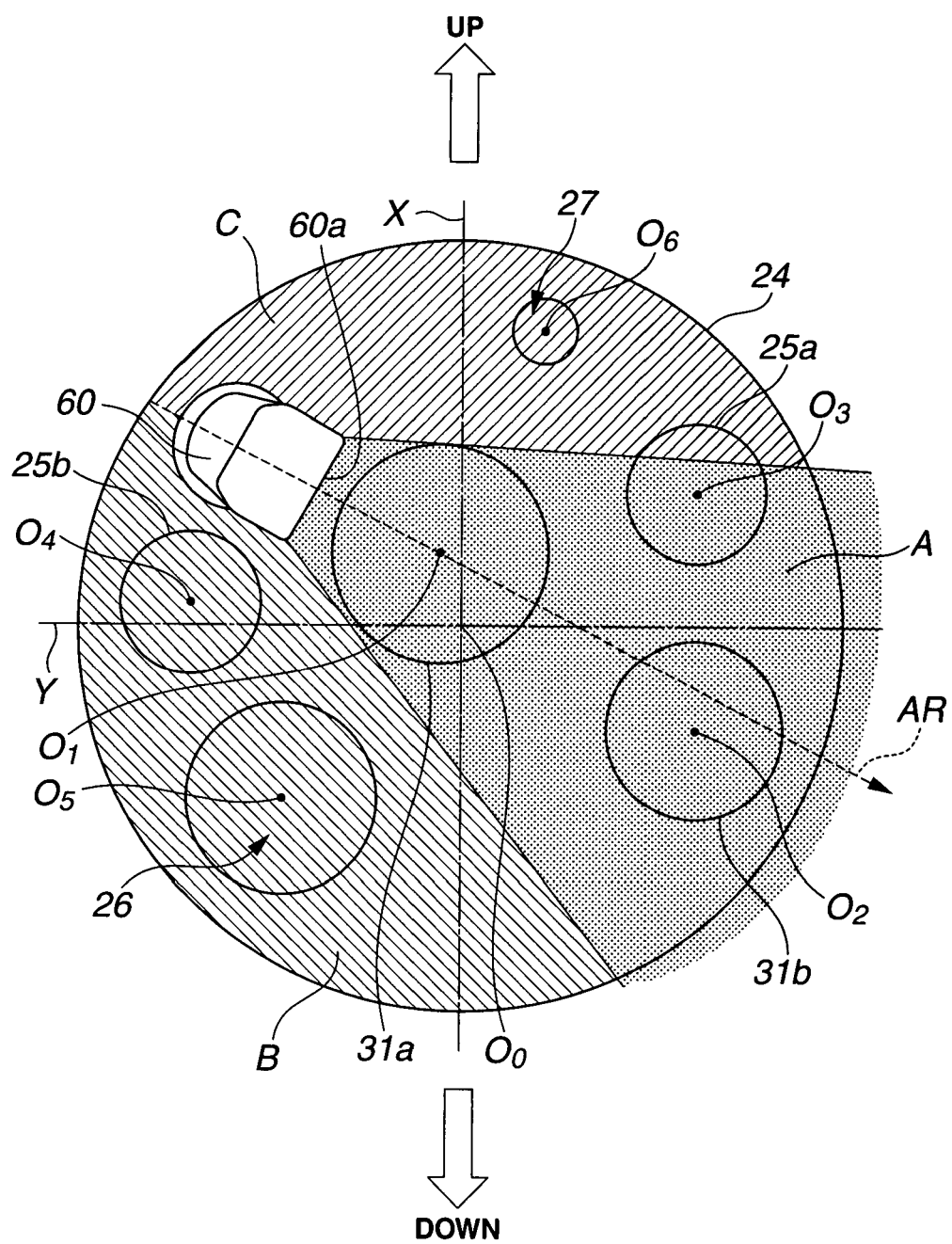
FIG. 13 is a plan view of the distal end cover as viewed from the front.

Next, referring to FIGS. 12 and 13, dispositions of the two illumination lenses 25*a*, 25*b*, the aperture portion 26 of the treatment instrument channel 19, and the aperture portion 27 of the forward water-feeding channel 20 disposed on the distal end cover 24 are described in detail.

As described above, on the distal end surface of the distal end cover 24, the two illumination lenses 25*a*, 25*b* are disposed at positions in the bending left/right direction to sandwich the observation lens 31*a* of the normal light image pickup unit 31A disposed at the generally center of the surface, the aperture portion 26 of the treatment instrument channel 19 is disposed at a position on a lower left side of the observation lens 31*a*, and the aperture portion 27 of the forward water-feeding channel 20 is disposed at a position on an upper right side of the observation lens 31*a*.

Also, as shown in FIG. 12, respective entire hole surfaces of the aperture portion 26 of the treatment instrument channel 19 and the aperture portion 27 of the forward water-feeding channel 20 are disposed on the distal end surface of the distal end cover 24 which is outside the gas/liquid spouting area A which is an area in which gas or liquid such as distilled water or air is spouted out in a spreading manner from the spouting port 60a of the air/water feeding nozzle 60.

In detail, as shown in FIG. 13, the aperture portion 26 of the treatment instrument channel 19 is disposed in an area B in the distal end surface of distal end cover 24, which is an area on a lower side of the distal end surface of the distal end cover 24 bisected along the arrow line AR indicating the spouting direction of gas or liquid such as distilled water or air from the spouting port 60a of the air/water feeding nozzle 60, and not including the spouting area A of the gas or liquid.

The aperture portion 27 of the forward water-feeding channel 20 is disposed in an area C on the distal end surface of the distal end cover 24, which is an area on an upper side of the distal end surface of the distal end cover 24 bisected along the arrow line AR, and not including the spouting area A of the gas or liquid.

In other words, on the distal end surface of the distal end cover 24, the aperture portions 26, 27 are respectively disposed at positions generally symmetric about the arrow line AR indicating the spouting direction of the gas or liquid such as distilled water or air. That is, the aperture portion 26, 27 are disposed on the distal end surface of the distal end cover 24 such that the center $O_5$ of the aperture portion 26 and the center $O_6$ of the aperture portion 27 are positioned apart from each other by a predetermined distance.

As described above, the endoscope 2 of the present embodiment can prevent the gas or liquid such as distilled water or air spouted out from the air/water feeding nozzle 60 from flowing into the aperture portions 26, 27, because the aperture portion 26 of the treatment instrument channel 19 and the aperture portion 27 of the forward water-feeding channel 20 are disposed in an area outside the gas/liquid spouting area A by the air/water feeding nozzle 60 on the distal end surface of the distal end cover 24.

This allows the gas or liquid such as distilled water or air spouted out from the air/water feeding nozzle 60 to be surely sprayed onto the observation lens 31b of the fluorescent light image pickup unit 31B on a farther side. As a result, the observation lens 31b of the fluorescent light image pickup unit 31B is surely and efficiently sprayed with the gas or liquid to be cleaned into a clean state, thus securing a good observation field of view.

Also, the aperture portion 26, 27 are disposed on the distal end surface of the distal end cover 24 such that the respective centers $O_5$, $O_6$ are apart from each other by a predetermined distance. This allows the endoscope 2 to spout out a liquid toward a diseased part in the body cavity, without being affected by the suction force to the aperture portion 26, when spouting out a liquid such as distilled water from the aperture portion 27 of the forward water-feeding channel 20 while performing sucking action from the aperture portion 26 through the treatment instrument channel 19. That is, the endoscope 2 of the present embodiment is configured to prevent the spouting direction of the liquid spouted out from the aperture portion 27 from being disturbed by the sucking from the aperture portion 26.

In the endoscope 2 of the present embodiment having the above-mentioned various characteristics (effects), the air/water feeding nozzle 60 provided on the distal end surface of the distal end cover 24, the observation lens 31a of the normal light image pickup unit 31A, and the observation lens 31b of the fluorescent light image capturing unit 31B are located on a generally straight line, and further the distal end cover 24 is provided with the stepped portion 24a having an outer surface in generally the same surface as the respective outer surfaces of the observation lenses 31a, 31b. Thus, by means of the single air/water feeding nozzle 60, the outer surfaces of the observation lenses 31a, 31b are sprayed with gas or liquid to be set in a clean state, thus secured of good observation field of view.

In particular, in the endoscope 2 that is frequently used for the normal light observation, the observation lens 31a with a larger lens diameter (caliber as outer diameter) which is easily adhered with body fluid, filth or the like is located closer to the air/water feeding nozzle 60, thus having improved cleanability and is secured of good observation field of view by normal light without being affected by decrease of cleaning power of gas or liquid such as distilled water or air spouted out from the spouting port 60a.

Note that the special light observation may be not only the fluorescent light observation but also that using a magnification optical system with a magnification of histological observation level (preferably not less than 100 times level) such as for cells and gland structure.

Furthermore, the present invention is not limited only to the above-described embodiment, but may be variously modified without departing from the spirit and scope of the invention.

What is claimed is:

1. An endoscope insertion portion comprising:
an insertion portion body having a distal end and a proximal end, the insertion portion body being configured to be inserted from the distal end into a body cavity;
a distal end portion provided at the distal end of the insertion portion body, the distal end portion having a distal end surface;
a plurality of image pickup portions, each of the plurality of image pickup portions being configured to observe light;
a plurality of observation windows, each of the plurality of observation windows having different outer diameters and being configured to lead incident light to a corresponding one of the plurality of image pickup portions, the plurality of observation windows being disposed on the distal end surface of the distal end portion;
an air/water feeding portion configured to spout out a gas or liquid toward the plurality of observation windows, the air/water feeding portion being disposed on the distal end portion;
a first aperture portion of a first duct into which a treatment instrument is insertable, the first aperture portion being disposed on the distal end surface of the distal end portion; and
a second aperture portion of a second duct for feeding a liquid to a region to be inspected, the second aperture portion being disposed on the distal end surface of the distal end portion;
wherein the plurality of observation windows are located to line up on a generally straight line in a spouting direction of the gas or liquid from the air/water feeding portion and one of the plurality of observation windows having the largest outer diameter is disposed on the distal end surface at a position closest to the air/water feeding portion than the other of the plurality of observation windows, and
the first aperture portion and the second aperture portion are disposed on the distal end surface outside a spouting area of the gas or liquid spouted out from the air/water feeding portion.

2. The endoscope insertion portion according to claim 1, wherein at least one of the plurality of image pickup portions is a first image pickup portion for performing normal light observation, and at least one is a second image pickup for performing special observation.

3. The endoscope insertion portion according to claim 2, wherein the special observation is fluorescent light observation.

4. The endoscope insertion portion according to claim 2, wherein the second image pickup portion can perform magnifying observation with a magnification larger than that of the first image pickup portion.

5. The endoscope insertion portion according to claim 3, wherein the second image pickup portion can perform magnifying observation with a magnification larger than that of the first image pickup portion.

6. An endoscope insertion portion comprising:
- an insertion portion body having a distal end and a proximal end, the insertion portion body being configured to be inserted from the distal end into a body cavity;
- a distal end portion provided at the distal end of the insertion portion body;
- a first image pickup portion configured to observe light;
- a second image pickup portion configured to observe light;
- an air/water feeding portion configured to spout out gas or liquid in a predetermined direction, the air/water feeding portion being disposed on the distal end portion;
- a first observation window configured to lead incident light to the first image pickup portion, the first observation window being disposed on the distal end portion on a side in the predetermined direction with respect to the air/water feeding portion;
- a second observation window configured to lead incident light to the second image pickup portion, the second observation window being disposed on the distal end portion on the side in the predetermined direction to line up on a generally straight line and to be positioned remoter from the air/water feeding portion with respect to the first observation window, the second observation window having an outer diameter smaller than that of the first observation window;
- a first aperture portion of a first duct into which a treatment instrument is insertable, the first aperture portion being disposed on the distal end portion and outside a spouting area of the gas or liquid spouted out from the air/water feeding portion; and
- a second aperture portion of a second duct for feeding a liquid to a region to be inspected, the second aperture portion being disposed on the distal end portion outside a spouting area of the gas or liquid spouted from the air/water feeding portion.

7. The endoscope insertion portion according to claim 6, wherein the first observation window receives incident light for performing normal light observation, and the second observation window receives incident light for performing special observation.

8. The endoscope insertion portion according to claim 7, wherein the special observation is fluorescent light observation.

9. The endoscope insertion portion according to claim 8, wherein the special observation is magnifying observation with a magnification larger than that of normal observation.

10. The endoscope insertion portion according to claim 7, wherein the special observation is magnifying observation with a magnification larger than that of normal observation.

* * * * *